(12) United States Patent
Goyal et al.

(10) Patent No.: US 12,094,582 B1
(45) Date of Patent: Sep. 17, 2024

(54) INTELLIGENT HEALTHCARE DATA FABRIC SYSTEM

(71) Applicant: Health At Scale Corporation, San Jose, CA (US)

(72) Inventors: Devendra Goyal, San Francisco, CA (US); Dahee Lee, San Jose, CA (US); Rudra Mehta, San Jose, CA (US); Tiange Zhan, Mountain View, CA (US); Zeeshan Syed, Cupertino, CA (US)

(73) Assignee: Health at Scale Corporation, San Jose, CA (US)

( * ) Notice: Subject to any disclaimer, the term of this patent is extended or adjusted under 35 U.S.C. 154(b) by 202 days.

(21) Appl. No.: 17/398,931

(22) Filed: Aug. 10, 2021

Related U.S. Application Data

(60) Provisional application No. 63/064,367, filed on Aug. 11, 2020.

(51) Int. Cl.
  *G16H 40/00* (2018.01)
  *G06N 20/00* (2019.01)
  (Continued)

(52) U.S. Cl.
  CPC ............ *G16H 10/60* (2018.01); *G06N 20/00* (2019.01); *G16H 20/00* (2018.01)

(58) Field of Classification Search
  CPC ........ G06Q 30/02; G16H 20/00; G16H 20/10; G16H 10/60; G06N 20/00
  See application file for complete search history.

(56) References Cited

U.S. PATENT DOCUMENTS

| | | |
|---|---|---|
| 7,191,150 B1 | 3/2007 | Shao |
| 7,853,456 B2 | 12/2010 | Soto et al. |

(Continued)

FOREIGN PATENT DOCUMENTS

| | | | |
|---|---|---|---|
| CA | 2560934 A1 * | 11/2005 | ............... A61B 5/00 |
| CA | 2715825 A1 | 8/2009 | |

(Continued)

OTHER PUBLICATIONS

Modin, Sonja; Tornkvist, Lena; Furhoff, Anna-Karin; Hylander, Ingrid, Family physician's effort to stay in charge of the medical treatment when patients have home care by district nurses. A grounded theory study (English), BMC Family Practice, 10,45, Jun. 22, 2009 (Year: 2009).*

(Continued)

*Primary Examiner* — Marilyn G Macasiano
(74) *Attorney, Agent, or Firm* — Morrison & Foerster LLP

(57) ABSTRACT

The present disclosure generally relates to generating a care and treatment plan for a patient using machine-learning techniques. An exemplary computer-implemented method comprises: receiving a plurality of care records; determining, based on a first machine learning model, that the plurality of care records are to be merged into an episode, wherein the episode is a predefined data representation comprising a predefined collection of data fields; identifying, from the plurality of care records, a plurality of attribute values corresponding to a particular attribute; determining, based on a second machine learning model, an aggregated attribute value based on the plurality of attribute values; updating, based on the aggregated attribute value, a data field of the episode; adding the episode to the patient profile, wherein the patient profile comprises a plurality of episodes associated with the patient.

20 Claims, 23 Drawing Sheets

(51) Int. Cl.
  *G16H 10/60* (2018.01)
  *G16H 20/00* (2018.01)

(56) References Cited

U.S. PATENT DOCUMENTS

| | | | |
|---|---|---|---|
| 8,417,541 B1 | 4/2013 | Kramer | |
| 8,548,937 B2 | 10/2013 | Saigal et al. | |
| 10,923,231 B2* | 2/2021 | Kelly | G16H 40/67 |
| 10,943,676 B2 | 3/2021 | Farooq et al. | |
| 11,114,204 B1 | 9/2021 | Guttag et al. | |
| 11,568,982 B1 | 1/2023 | Guttag et al. | |
| 11,610,679 B1* | 3/2023 | Zhan | G06N 3/096 |
| 2003/0135128 A1 | 7/2003 | Suffin | |
| 2004/0107088 A1 | 6/2004 | Budzinski | |
| 2006/0173663 A1 | 8/2006 | Langheier | |
| 2006/0206359 A1 | 9/2006 | Stang | |
| 2007/0088577 A1 | 4/2007 | Carter et al. | |
| 2007/0269804 A1 | 11/2007 | Liew | |
| 2009/0093689 A1 | 4/2009 | Schuppert et al. | |
| 2009/0259550 A1 | 10/2009 | Mihelich | |
| 2010/0184093 A1 | 7/2010 | Donovan | |
| 2011/0082712 A1 | 4/2011 | Eberhardt, III | |
| 2011/0295621 A1 | 12/2011 | Farooq et al. | |
| 2012/0041330 A1 | 2/2012 | Prichep et al. | |
| 2012/0066217 A1 | 3/2012 | Eder | |
| 2012/0095943 A1 | 4/2012 | Yankov | |
| 2012/0109683 A1 | 5/2012 | Ebadollahi | |
| 2012/0179002 A1 | 7/2012 | Brunetti et al. | |
| 2013/0022953 A1 | 1/2013 | Van Der Linden | |
| 2013/0096948 A1 | 4/2013 | Parkinson | |
| 2013/0185096 A1 | 7/2013 | Giusti | |
| 2013/0197925 A1 | 8/2013 | Blue | |
| 2013/0225439 A1 | 8/2013 | Princen et al. | |
| 2014/0058755 A1 | 2/2014 | Macoviak | |
| 2014/0108034 A1 | 4/2014 | Akbay | |
| 2014/0200824 A1 | 7/2014 | Pancoska | |
| 2014/0257838 A1* | 9/2014 | Karra | G16H 20/00 705/2 |
| 2014/0371610 A1 | 12/2014 | Liu et al. | |
| 2015/0006456 A1 | 1/2015 | Sudharsan | |
| 2015/0046181 A1 | 2/2015 | Adjaoute | |
| 2015/0073943 A1 | 3/2015 | Norris et al. | |
| 2015/0100336 A1 | 4/2015 | Ford et al. | |
| 2015/0100349 A1 | 4/2015 | Lacy et al. | |
| 2015/0161331 A1 | 6/2015 | Oleynik | |
| 2015/0164453 A1 | 6/2015 | Choi et al. | |
| 2015/0248534 A1 | 9/2015 | Krzywicki et al. | |
| 2015/0278470 A1 | 10/2015 | Bakker | |
| 2015/0289795 A1 | 10/2015 | Batlle Gómez | |
| 2015/0294075 A1 | 10/2015 | Rinaldo | |
| 2015/0317449 A1 | 11/2015 | Eder | |
| 2015/0367145 A1 | 12/2015 | Sjölund et al. | |
| 2016/0012202 A1 | 1/2016 | Hu et al. | |
| 2016/0085937 A1* | 3/2016 | Dettinger | G16H 20/10 705/2 |
| 2016/0135706 A1 | 5/2016 | Sullivan et al. | |
| 2016/0147959 A1 | 5/2016 | Mariottini et al. | |
| 2016/0196398 A1 | 7/2016 | Vivero et al. | |
| 2016/0203217 A1 | 7/2016 | Anisingaraju et al. | |
| 2016/0232310 A1* | 8/2016 | Dunn | G16H 50/20 |
| 2016/0259883 A1 | 9/2016 | Grinchuk et al. | |
| 2016/0378943 A1 | 12/2016 | Vallée | |
| 2017/0073761 A1 | 3/2017 | Harkin et al. | |
| 2017/0083682 A1 | 3/2017 | Mcnutt | |
| 2017/0101093 A1 | 4/2017 | Barfield, Jr. et al. | |
| 2017/0124269 A1 | 5/2017 | Mcnair | |
| 2017/0177822 A1* | 6/2017 | Fogel | G16H 50/20 |
| 2017/0185723 A1 | 6/2017 | Mccallum et al. | |
| 2017/0277856 A1 | 9/2017 | De La Torre et al. | |
| 2017/0308671 A1 | 10/2017 | Bahrami et al. | |
| 2017/0316180 A1 | 11/2017 | Takeda et al. | |
| 2018/0121619 A1 | 5/2018 | Perlroth et al. | |
| 2018/0214105 A1 | 8/2018 | Anavi et al. | |
| 2018/0271455 A1* | 9/2018 | Zhong | A61B 5/0004 |
| 2019/0043606 A1 | 2/2019 | Roots et al. | |
| 2019/0172587 A1 | 6/2019 | Park et al. | |
| 2019/0333613 A1 | 10/2019 | Zaidi et al. | |
| 2019/0371450 A1 | 12/2019 | Lou et al. | |
| 2020/0074313 A1 | 3/2020 | Sharifi Sedeh et al. | |
| 2021/0035693 A1 | 2/2021 | Mohammad et al. | |
| 2021/0065909 A1 | 3/2021 | Donaldson | |
| 2021/0090748 A1 | 3/2021 | Toyoshiba et al. | |
| 2021/0118559 A1 | 4/2021 | Lefkofsky | |
| 2021/0221404 A1 | 7/2021 | Reiner et al. | |
| 2021/0249138 A1 | 8/2021 | Hayashitani et al. | |

FOREIGN PATENT DOCUMENTS

| | | | |
|---|---|---|---|
| EP | 3382584 A1 | 10/2018 | |
| EP | 3500999 A1 * | 6/2019 | G06Q 50/22 |
| JP | 2017174406 A | 9/2017 | |
| WO | WO 2001/070094 A2 * | 9/2001 | A61B 5/00 |
| WO | 2015157576 A1 | 10/2015 | |
| WO | WO 2016/044514 A1 * | 3/2016 | G16H 10/60 |
| WO | 2016120955 A1 | 8/2016 | |
| WO | WO 2017/072651 A1 * | 5/2017 | G06Q 10/06 |
| WO | 2019212005 A1 | 11/2019 | |
| WO | 2020081609 A1 | 4/2020 | |

OTHER PUBLICATIONS

Herrete, Emily; Gallagher, Krishnan; Forbes, Harriet; Mathur, Rohini; van Staa, Tjeerd; Smeeth, Liam, Data Resource Profile: Clinical practice Research Datalink (CPRD) (English), International Journal of Epidemiology, 44(3), 827-836, Jun. 1, 2015 (Year: 2015).*

Alvarez Bustins, Gerard; Lopez Plaza, Pedro-Victor; Carvajal, Sonia Roura, Profile of osteophatic in Spain: results from a starndard data collection study (English), BMC Complementary and Alternative Medicine, 18/, 129, Apr. 11, 2018 (Year: 2018).*

Subhra Shriti Mishra; Akhtar Rasool, IoT Health care Monitoring and Tracking: A Survey (English), 2019 3rd International Conference on Trends in Electronics and Informatics (ICOEI) (pp. 1052-1057), Oct. 25, 2019 (Year: 2019).*

Baechle, C., et al., "Latent topic ensemble learning for hospital readmission cost optimization," European Journal of Operational Research 281 (2020) 517-531. (Year: 2019).

Non-Final Office Action mailed Feb. 8, 2022, for U.S. Appl. No. 16/853,621, filed Apr. 20, 2020, 27 pages.

Rahimian, F., et al., "Predicting the risk of emergency admission with machine learning: Development and validation using linked electronic health records," PLOS Medicine, Nov. 20, 2018, pp. 1-18 (Year: 2018).

Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).

Caruana, Rich. (1997). "Multitask Learning," Kluwer Academic Publishers, Manufactured in the Netherlands, Machine Learning, 35 pages.

Caruana, Rich. (May 1996). "Algorithms and Applications for Multitask Learning," School of Computer Science, Carnegie Mellon University, Pittsburgh, PA, 9 pages.

Final Office Action mailed Dec. 21, 2020, for U.S. Appl. No. 14/622,112, filed Feb. 13, 2015, nine pages.

Final Office Action mailed Dec. 26, 2018, for U.S. Appl. No. 14/809,528, filed Jul. 27, 2015, 30 pages.

Final Office Action mailed Jan. 7, 2019, for U.S. Appl. No. 14/736,470, filed Jun. 11, 2015, fifteen pages.

Final Office Action mailed Jul. 21, 2020, for U.S. Appl. No. 14/678,349, filed Apr. 3, 2015, twelve pages.

Final Office Action mailed Jul. 21, 2020, for U.S. Appl. No. 14/809,528, filed Jul. 27, 2015, twenty pages.

Final Office Action mailed Jul. 23, 2018, for U.S. Appl. No. 14/622,112, filed Feb. 13, 2015, eleven pages.

Final Office Action mailed May 3, 2018, for U.S. Appl. No. 14/678,349, filed Apr. 3, 2015, twenty one pages.

Final Office Action mailed Nov. 16, 2020, for U.S. Appl. No. 14/736,470, filed Jun. 11, 2015, eleven bages.

(56) References Cited

OTHER PUBLICATIONS

Non-Final Office Action mailed Aug. 17, 2021, for U.S. Appl. No. 14/622,112, filed Feb. 13, 2015, 11 pages.
Non-Final Office Action mailed Aug. 27, 2021, for U.S. Appl. No. 14/809,528, filed Jul. 27, 2015, 14 pages.
Non-Final Office Action mailed Dec. 18, 2019, for U.S. Appl. No. 14/678,349, filed Apr. 3, 2015, eleven pages.
Non-Final Office Action mailed Feb. 26, 2018, for U.S. Appl. No. 14/736,470, filed Jun. 11, 2015, sixteen pages.
Non-Final Office Action mailed Jan. 10, 2019, for U.S. Appl. No. 14/678,349, filed Apr. 3, 2015, twenty WO pages.
Non-Final Office Action mailed Jan. 29, 2020, for U.S. Appl. No. 14/809,528, filed Jul. 27, 2015, 20 pages.
Non-Final Office Action mailed Jan. 29, 2021, for U.S. Appl. No. 14/678,349, filed Apr. 3, 2015, eight pages.
Non-Final Office Action mailed Mar. 14, 2019, for U.S. Appl. No. 14/622,112, filed Feb. 13, 2015, ten pages.
Non-Final Office Action mailed Mar. 27, 2020, for U.S. Appl. No. 14/622,112, filed Feb. 13, 2015, hine pages.
Non-Final Office Action mailed Mar. 9, 2020, for U.S. Appl. No. 14/736,470, filed Jun. 11, 2015, nine pages.
Non-Final Office Action mailed May 1, 2018, for U.S. Appl. No. 14/809,528, filed Jul. 27, 2015, 25 pages.
Non-Final Office Action mailed Sep. 22, 2017, for U.S. Appl. No. 14/678,349, filed Apr. 3, 2015, thirteen pages.
Non-Final Office Action mailed Sep. 28, 2017, for U.S. Appl. No. 14/622,112, filed Feb. 13, 2015, fifteen pages.
Notice of Allowance mailed Jul. 28, 2021, for U.S. Appl. No. 14/678,349, filed Apr. 3, 2015, eleven pages.
Brakenhoff, T. B., et al. (2018). "Investigating Risk Adjustment Methods for Health Care Provider Profiling When Observations are Scarce or Events Rare". Health Services Insights, vol. 11, 1-10, doi: http://dx.doi.org/10.1177/1178632918785133 , (Year:2018).
Final Office Action mailed Jul. 12, 2022, for U.S. Appl. No. 16/853,621, filed Apr. 20, 2020, twenty three pages.
Final Office Action mailed May 18, 2023, for U.S. Appl. No. 16/875,835, filed May 15, 2020, 55 pages.
Final Office Action mailed Oct. 4, 2022, for U.S. Appl. No. 14/736,470, filed Jun. 11, 2015, thirteen pages.
Li, Xiuli et al., "Lung Nodule Malignancy Prediction Using Multi-task Convolutional Neural Network," Proc. of SPIE vol. 10134, 1013424-1 (Year: 2017).
Non-Final Office Action mailed Dec. 14, 2022, for U.S. Appl. No. 14/809,528, filed Jul. 27, 2015, fifteen pages.
Non-Final Office Action mailed Jan. 18, 2023, for U.S. Appl. No. 17/392,086, filed Aug. 2, 2021, nineteen pages.
Non-Final Office Action mailed Jul. 27, 2022, for U.S. Appl. No. 16/875,835, filed May 15, 2020, 48 pages.
Non-Final Office Action mailed Mar. 18, 2022, for U.S. Appl. No. 14/736,470, filed Jun. 11, 2015, 14 pages.
Notice of Allowance mailed Feb. 2, 2023, for U.S. Appl. No. 16/853,621, filed Apr. 20, 2020, sixteen pages.
Notice of Allowance mailed Nov. 7, 2022, for U.S. Appl. No. 14/622,112, filed Feb. 13, 2015, nine pages.
Notice of Allowance mailed Sep. 6, 2022, for U.S. Appl. No. 14/622,112, filed Feb. 13, 2015, nine pages.
Ruder, Sebastian. "An Overview of Multi-Task Learning in Deep Neural Networks," https://ruder.io/multi-task/ (Year: 2017).
Tan, Kar Way. "Dynamic Queue Management for Hospital Emergency Room Services." Order No. 10169843 Singapore Management University (Singapore), 2013. Ann Arbor: ProQuest. Web., Aug. 25, 2022. (Year: 2013).
Non-Final Office Action mailed Sep. 27, 2023, for U.S. Appl. No. 16/875,835, filed May 15, 2020, 73 pages.

\* cited by examiner

Augmented Care Records 300

|  | Record Attributes | Provider Attributes | Patient Attributes | ... |
|---|---|---|---|---|
| Care Record 1 | ... | Provider X | Patient A | ... |
| Care Record 2 | ... | Provider Y | Patient B | ... |
| Care Record 3 | ... | Provider Y | Patient A | ... |
| Care Record 4 | ... | Provider Z | Patient A | ... |
| Care Record 5 | ... | Provider X | Patient C | ... |
| Care Record 6 | ... | Provider V | Patient A | ... |
| Care Record 7 | ... | Provider W | Patient B | ... |

FIG. 3A

Episodes of Care 302

| | Aggregate Record Attributes | Provider Attributes | Patient Attributes | Noise/Error Probability |
|---|---|---|---|---|
| Episode 1 | ... | Provider Y | Patient A | 0.4 |
| Episode 2 | ... | Provider V | Patient A | 0.1 |
| Episode 3 | ... | Provider W | Patient B | 0.9 |
| Episode 4 | ... | Provider X | Patient C | 0.1 |
| Episode 5 | ... | Provider V | Patient D | 0.05 |
| Episode 6 | ... | Provider W | Patient D | 0.02 |

FIG. 3C

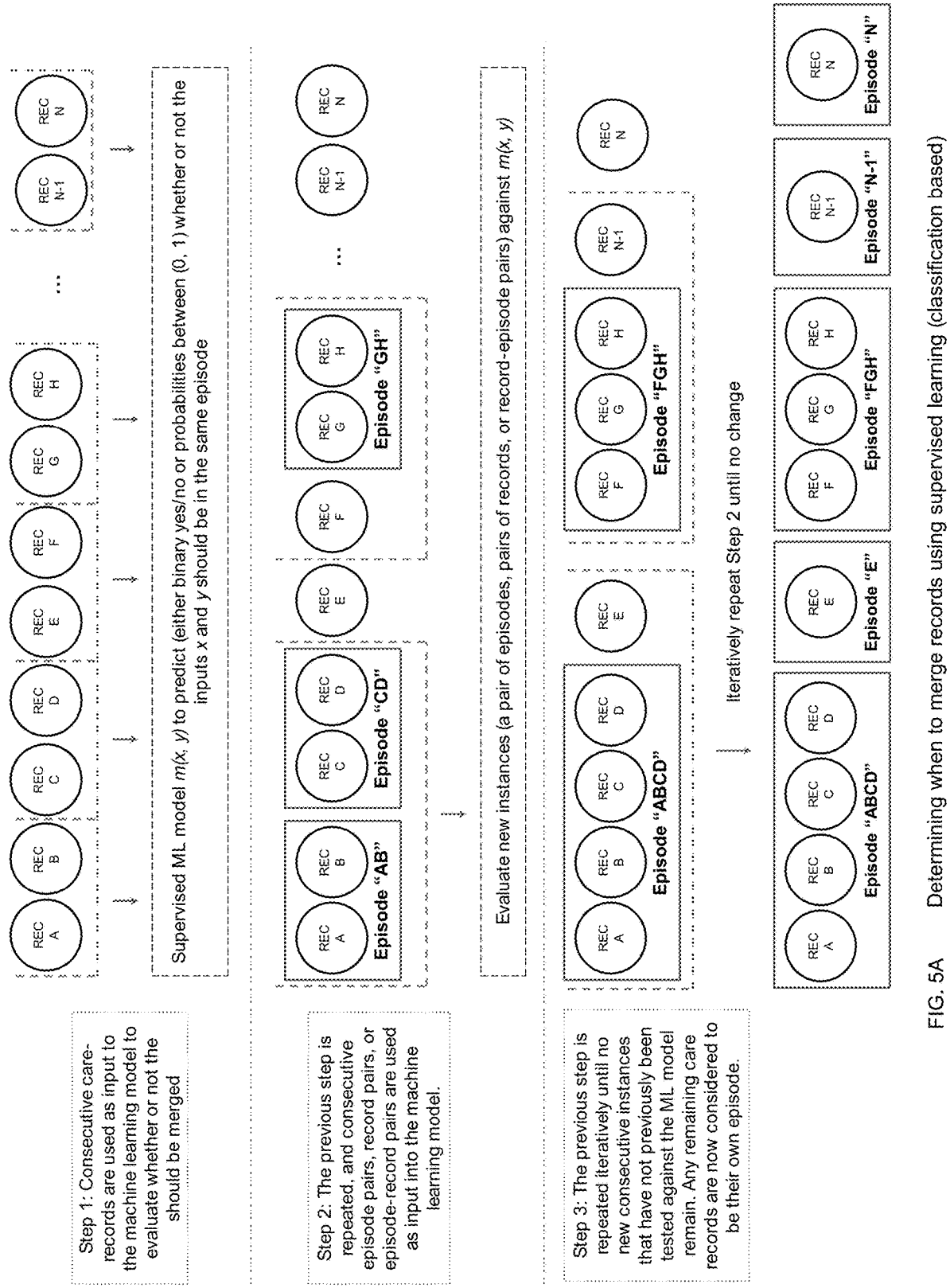
FIG. 5A  Determining when to merge records using supervised learning (classification based)

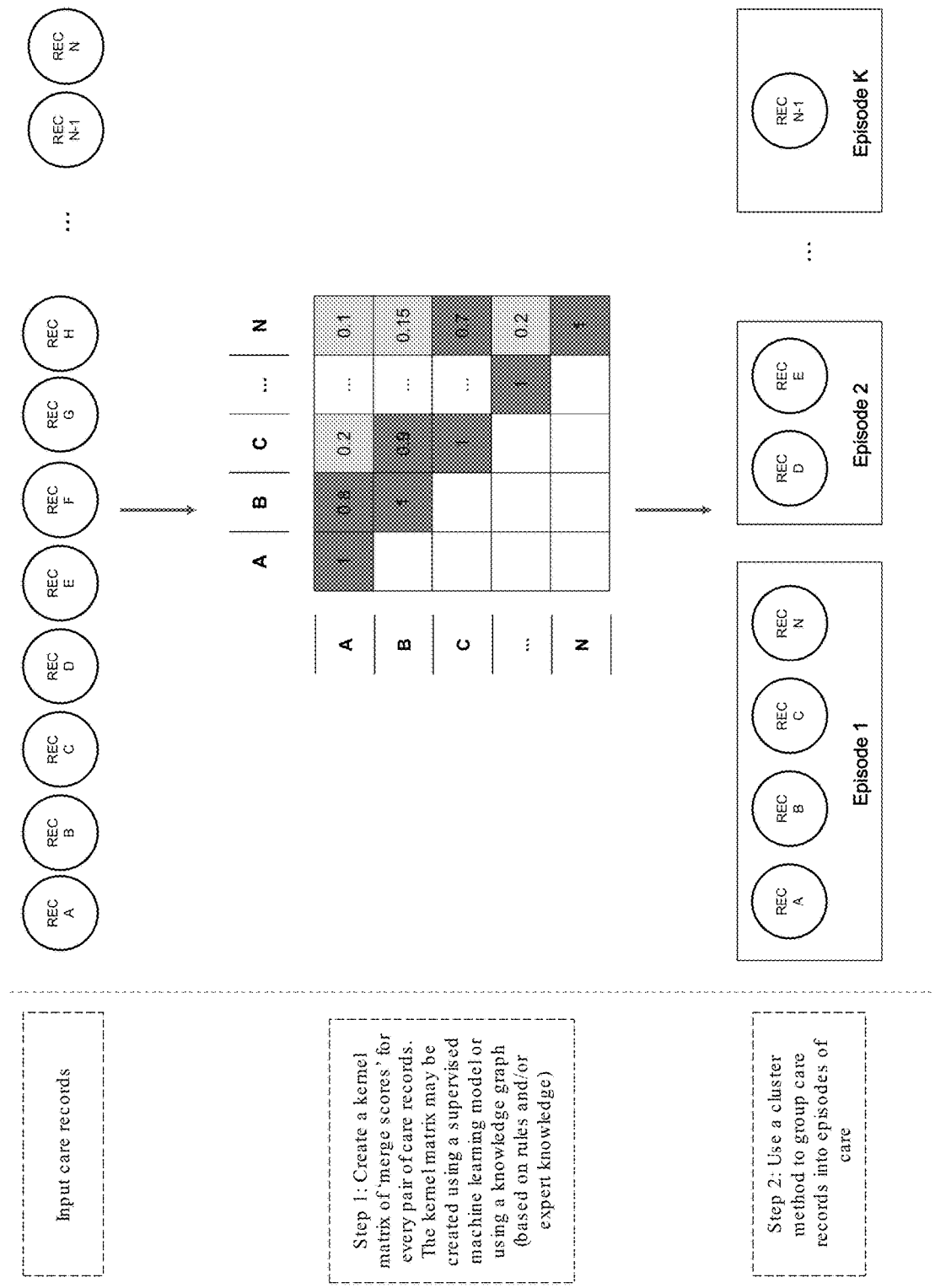
Figure 5B: Determining when to merge records using supervised learning (clustering based)

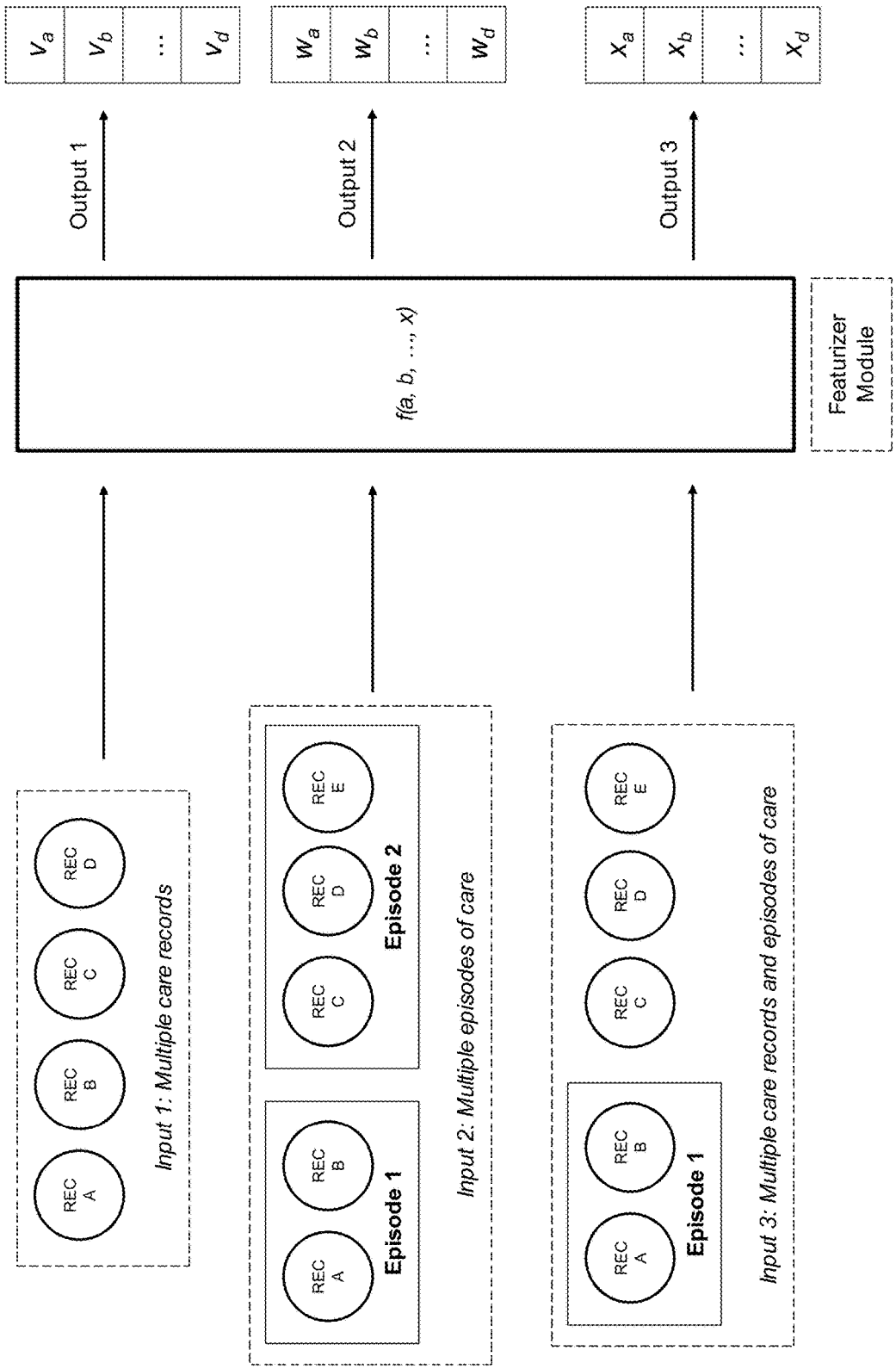
Figure 5C: Featurizing a plurality of care records, episodes of care, or some combination thereof into a single feature vector

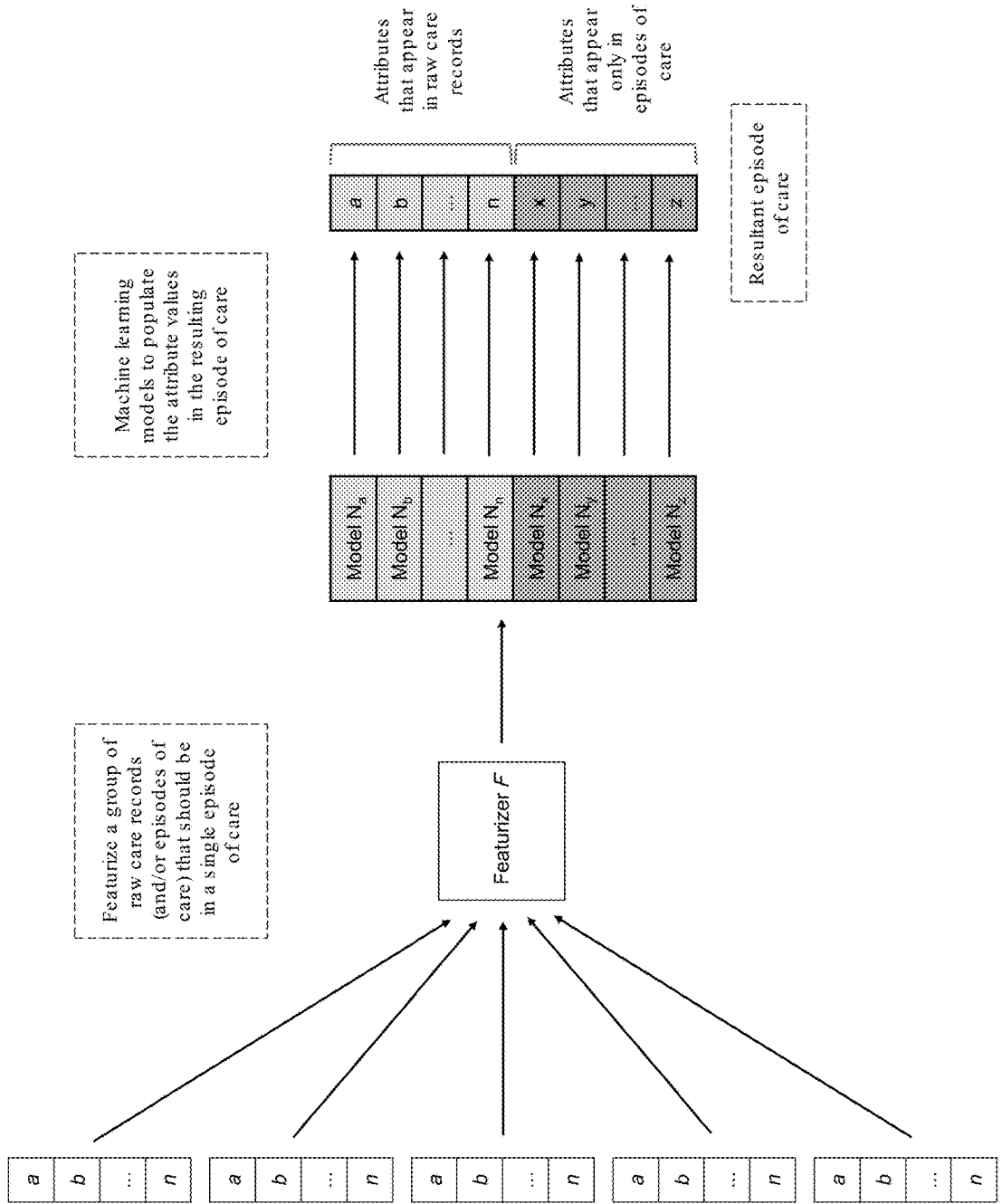
Figure 6: Determining how to merge records using machine learning

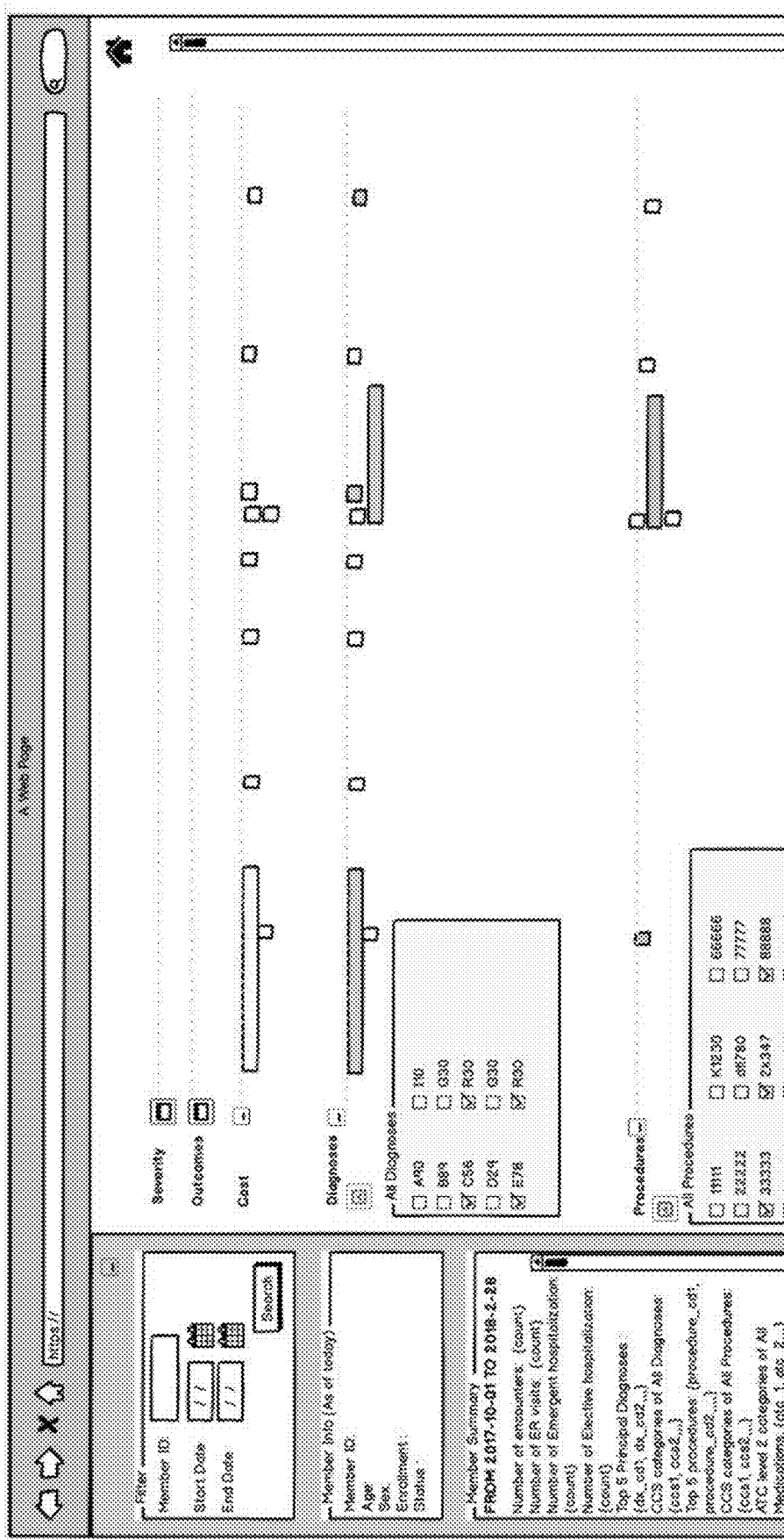
FIG. 8A (Visualization: Member View with filtered attributes)

FIG. 9: Visualization: Visualizing raw care records

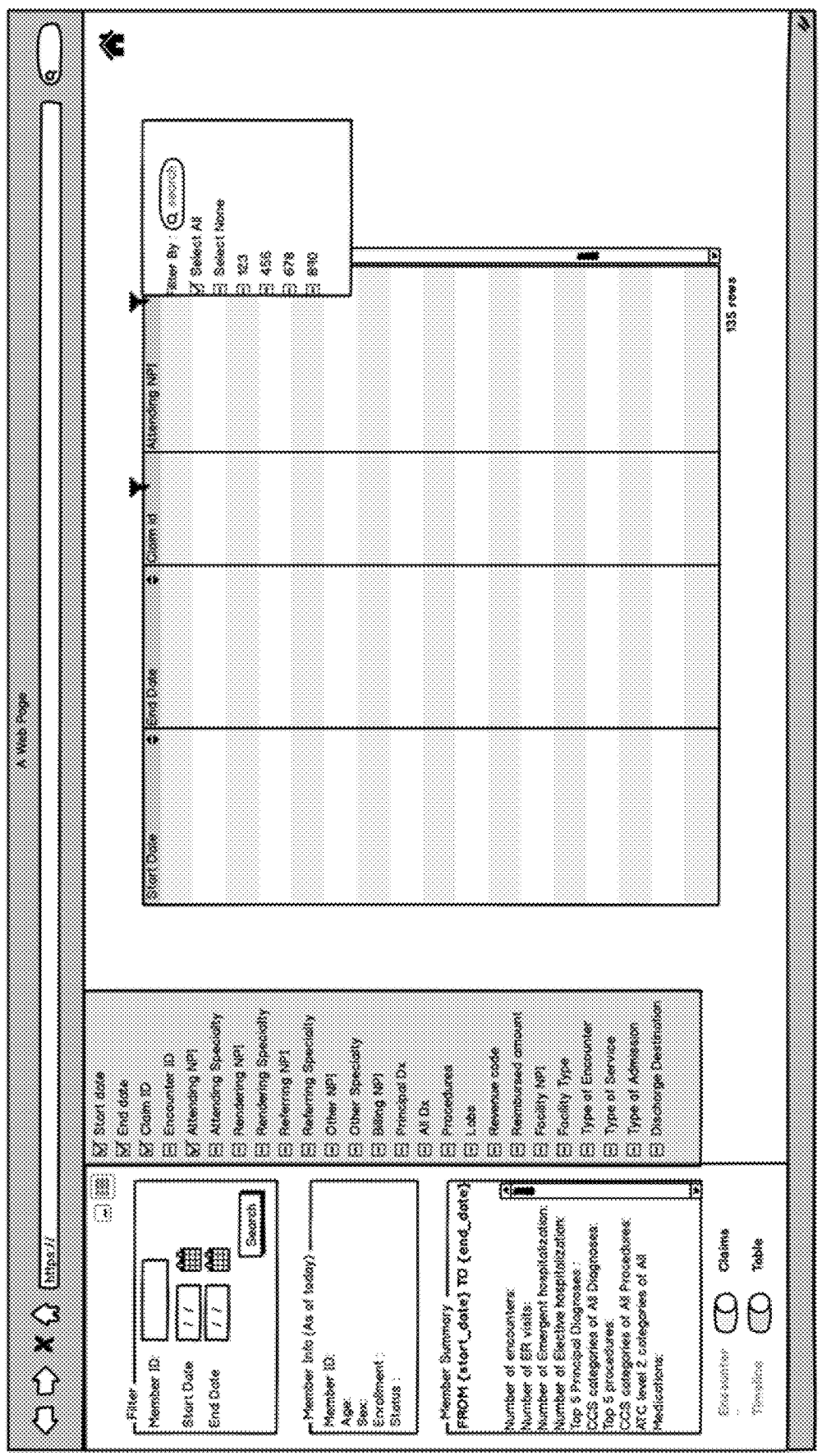
FIG. 10: Visualization: Visualizing raw care records with optional filters

1100

1102
RECEIVING A PLURALITY OF CARE RECORDS

1104
DETERMINING, BASED ON A FIRST MACHINE LEARNING MODEL, THAT THE PLURALITY OF CARE RECORDS ARE TO BE MERGED INTO AN EPISODE, WHEREIN THE EPISODE IS A PREDEFINED DATA REPRESENTATION COMPRISING A PREDEFINED COLLECTION OF DATA FIELDS

1106
IDENTIFYING, FROM THE PLURALITY OF CARE RECORDS, A PLURALITY OF ATTRIBUTE VALUES CORRESPONDING TO A PARTICULAR ATTRIBUTE

1108
DETERMINING, BASED ON A SECOND MACHINE LEARNING MODEL, AN AGGREGATED ATTRIBUTE VALUE BASED ON THE PLURALITY OF ATTRIBUTE VALUES

1110
UPDATING, BASED ON THE AGGREGATED ATTRIBUTE VALUE, A DATA FIELD OF THE EPISODE

1112
ADDING THE EPISODE TO THE PATIENT PROFILE, WHEREIN THE PATIENT PROFILE COMPRISES A PLURALITY OF EPISODES ASSOCIATED WITH THE PATIENT

FIG. 11

INTELLIGENT HEALTHCARE DATA FABRIC SYSTEM

CROSS-REFERENCE TO RELATED APPLICATIONS

This application claims priority to U.S. Provisional Application No. 63/064,367, filed Aug. 11, 2020, the contents of which are incorporated by reference herein in their entirety.

FIELD OF THE INVENTION

The present disclosure relates generally to an intelligent healthcare data fabric system, and more specifically to generation and usage of high-level healthcare data representations (e.g., patient profiles, healthcare provider profiles and their associated episodes of care) using techniques such as expert-defined rules, machine learning algorithms or both.

BACKGROUND

Patients, healthcare providers, payers, and pharmaceutical companies generate a myriad of raw healthcare data, such as claims data, clinical (EHR) data, wearable data, self-reported patient data, omics data, imaging data, social determinants of health data, demographic data, administrative data, and economic data.

However, raw healthcare data can often be fragmented, noisy, and/or biased. For example, raw healthcare data can be generated for various services (e.g., clinic visits, lab tests, surgeries, drugs, hospital/nursing home stays), and these various services can be provided in various settings (e.g., hospitals, nursing facilities, ambulatory centers, clinics, labs) in an inpatient or outpatient basis. Further, different providers (e.g., individual physicians, hospitals, networks) may be involved across the various services and settings and generate data for their portions of care. Data generated by different providers, for different services, and in different settings can vary significantly in format, organization, taxonomy (e.g., standards, procedures). Further, the raw healthcare data can be affected by noise and bias.

BRIEF SUMMARY

An exemplary computer-implemented method for generating a care and treatment plan for a patient comprises: (a) receiving an initial series of care records; (b) generating a first plurality of care data groups based on the initial series of care records, each care data group comprising at least two care records from the initial series; (c) generating a feature vector for each care data group of the first plurality of care data groups to obtain a first plurality of feature vectors; (d) inputting each feature vector of the first plurality of feature vectors into a trained machine-learning model to determine if a care data group is to be merged into a single medical episode to identify a new series of care records, medical episodes, or a combination thereof; (e) generating a second plurality of care data groups based on the new series, each care data group comprising at least: two care records, two medical episodes, or a care record and a medical episode; (f) generating a feature vector for each care data group of the second plurality of care data groups to obtain a second plurality of feature vectors; (g) inputting each feature vector of the second plurality of feature vectors into the trained machine-learning model to determine if a care data group is to be merged into a single medical episode to update the new series of care records, medical episodes, or a combination thereof; (h) repeating steps (e)-(g) zero or more times using the new series to identify a final series of medical episodes, wherein each medical episode of the final series of medical episodes corresponds to one or more care records in the initial series of care records; and (i) creating a patient profile for the patient, the patient profile comprising at least a subset of the final series of medical episodes; and (j) generating the care and treatment plan for the patient based on the patient profile.

In some embodiments, the care and treatment plan comprises: coordination, recommendation, or administration of one or more treatments or care services for the patient.

In some embodiments, the one or more treatments or care services comprise: a medication, a procedure, an intervention, a test, a service, a lifestyle change, a behavior, a diagnosis, a prognosis, or a combination thereof.

In some embodiments, the method further comprises: evaluating a medical claim or a proposed treatment based on the patient profile for eligibility, prior authorization, or approval.

In some embodiments, determining the care and treatment plan comprises: training a predictive machine-learning model using a plurality of medical episodes corresponding to patients similar to the patient; and determining an effect of care and treatment based on the trained predictive machine-learning model.

In some embodiments, the predictive model is configured to output a predicted outcome of the care and treatment.

In some embodiments, repeating steps (e)-(g) comprises repeating steps (e)-(g) until none of the care data groups can be merged.

In some embodiments, the machine-learning model is trained using a first training dataset comprising: features of a plurality of groups of care records; and for each group of care records, a label indicating whether or not the respective group of care records can be merged.

In some embodiments, the method further comprises: obtaining a label corresponding to a group of care records by querying a user using an active learning framework.

In some embodiments, the machine-learning model is a first machine-learning model, the method further comprising: after identifying a care data group that is to be merged into a single medical episode identifying a plurality of attribute values corresponding to an attribute from the care data group; determining, based on a second machine-learning model, an aggregated attribute value based on the plurality of attribute values; merging the care data group by generating a medical episode and assigning the aggregated attribute value to a data field of the generated medical episode.

In some embodiments, the second machine-learning model is trained using a second training dataset comprising: features of a plurality of groups of care records; and for each group of care records, an aggregate attribute value of the particular attribute.

In some embodiments, the method further comprises: obtaining a label corresponding to a group of care records and one or more attributes by querying a user using an active learning framework.

In some embodiments, the method further comprises: determining, based on a third machine-learning model, one or more noise probabilities for the generated episode.

In some embodiments, the method further comprises: updating the generated medical episode based on the one or more noise probabilities.

In some embodiments, the method further comprises: adding an episode of the final series of medical episodes to a provider profile, wherein the provider profile comprises a plurality of episodes associated with a provider.

In some embodiments, the method further comprises: adding an episode of the final series of medical episodes to a patient profile, wherein the patient profile comprises a plurality of episodes associated with a patient.

In some embodiments, the series of care records comprises health care claims data, clinical (EHR) data, wearable data, self-reported patient data, omics data, imaging data, social determinants of health data, demographic data, administrative data, economic data, device data, lab data, or any combination thereof.

In some embodiments, the method further comprises: augmenting the series of data records with provider metadata and patient metadata.

An exemplary system for generating a care and treatment plan for a patient comprises: one or more processors; a memory; and one or more programs, wherein the one or more programs are stored in the memory and configured to be executed by the one or more processors, the one or more programs including instructions for: (a) receiving an initial series of care records; (b) generating a first plurality of care data groups based on the initial series of care records, each care data group comprising at least two care records from the initial series; (c) generating a feature vector for each care data group of the first plurality of care data groups to obtain a first plurality of feature vectors; (d) inputting each feature vector of the first plurality of feature vectors into a trained machine-learning model to determine if a care data group is to be merged into a single medical episode to identify a new series of care records, medical episodes, or a combination thereof; (e) generating a second plurality of care data groups based on the new series, each care data group comprising at least: two care records, two medical episodes, or a care record and a medical episode; (f) generating a feature vector for each care data group of the second plurality of care data groups to obtain a second plurality of feature vectors; (g) inputting each feature vector of the second plurality of feature vectors into the trained machine-learning model to determine if a care data group is to be merged into a single medical episode to update the new series of care records, medical episodes, or a combination thereof; (h) repeating steps (c)-(g) zero or more times using the new series to identify a final series of medical episodes, wherein each medical episode of the final series of medical episodes corresponds to one or more care records in the initial series of care records; and (i) creating a patient profile for the patient, the patient profile comprising at least a subset of the final series of medical episodes; and (j) generating the care and treatment plan for the patient based on the patient profile.

An exemplary non-transitory computer-readable storage medium stores one or more programs for generating a care and treatment plan for a patient, the one or more programs comprising instructions, which when executed by one or more processors of an electronic device, cause the electronic device to: (a) receive an initial series of care records; (b) generate a first plurality of care data groups based on the initial series of care records, each care data group comprising at least two care records from the initial series; (c) generate a feature vector for each care data group of the first plurality of care data groups to obtain a first plurality of feature vectors; (d) input each feature vector of the first plurality of feature vectors into a trained machine-learning model to determine if a care data group is to be merged into a single medical episode to identify a new series of care records, medical episodes, or a combination thereof; (e) generate a second plurality of care data groups based on the new series, each care data group comprising at least: two care records, two medical episodes, or a care record and a medical episode; (f) generate a feature vector for each care data group of the second plurality of care data groups to obtain a second plurality of feature vectors; (g) input each feature vector of the second plurality of feature vectors into the trained machine-learning model to determine if a care data group is to be merged into a single medical episode to update the new series of care records, medical episodes, or a combination thereof; (h) repeat steps (c)-(g) zero or more times using the new series to identify a final series of medical episodes, wherein each medical episode of the final series of medical episodes corresponds to one or more care records in the initial series of care records; and (i) create a patient profile for the patient, the patient profile comprising at least a subset of the final series of medical episodes; and (j) generate the care and treatment plan for the patient based on the patient profile.

An exemplary computer-implemented method for generating a patient profile of a patient, comprising: receiving a plurality of care records; determining, based on a first machine learning model, that the plurality of care records are to be merged into an episode, wherein the episode is a predefined data representation comprising a predefined collection of data fields; identifying, from the plurality of care records, a plurality of attribute values corresponding to a particular attribute; determining, based on a second machine learning model, an aggregated attribute value based on the plurality of attribute values; updating, based on the aggregated attribute value, a data field of the episode; adding the episode to the patient profile, wherein the patient profile comprises a plurality of episodes associated with the patient.

In some embodiments, the first machine learning model is trained using a first training dataset comprising: features of a plurality of groups of care records; and for each group of care records, a label indicating whether or not the respective group of care records are to be merged.

In some embodiments, the method further comprises: obtaining a label corresponding to a group of care records by querying a user using an active learning framework.

In some embodiments, the second machine learning model is trained using a second training dataset comprising: features of a plurality of groups of care records; and for each group of care records, an attribute value of the particular attribute that may be an aggregate, summary, average, etc.

In some embodiments, the method further comprises: obtaining a label corresponding to a group of care records and one or more attributes by querying a user using an active learning framework.

In some embodiments, the method further comprises: determining, based on a third machine learning model, one or more noise probabilities for the episode.

In some embodiments, the method further comprises: updating the episode based on the one or more noise probabilities.

In some embodiments, the method further comprises: adding the episode to a provider profile, wherein the provider profile comprises a plurality of episodes associated with the provider.

In some embodiments, the plurality of care records comprises medical claims data, clinical (EHR) data, wearable data, self-reported patient data, omics data, imaging data, social determinants of health data, demographic data, administrative data, economic data, or any combination thereof.

In some embodiments, the method further comprises: augmenting the plurality of care records with provider metadata and patient metadata.

An exemplary electronic device comprises: one or more processors; a memory; and one or more programs, wherein the one or more programs are stored in the memory and configured to be executed by the one or more processors, the one or more programs including instructions for: receiving a plurality of care records; determining, based on a first machine learning model, that the plurality of care records are to be merged into an episode, wherein the episode is a predefined data representation comprising a predefined collection of data fields; identifying, from the plurality of care records, a plurality of attribute values corresponding to a particular attribute; determining, based on a second machine learning model, an aggregated attribute value based on the plurality of attribute values; updating, based on the aggregated attribute value, a data field of the episode; adding the episode to the patient profile, wherein the patient profile comprises a plurality of episodes associated with the patient.

An exemplary non-transitory computer-readable storage medium stores one or more programs, the one or more programs comprising instructions, which when executed by one or more processors of an electronic device having a display, cause the electronic device to: receiving a plurality of care records; determining, based on a first machine learning model, that the plurality of care records are to be merged into an episode, wherein the episode is a predefined data representation comprising a predefined collection of data fields; identifying, from the plurality of care records, a plurality of attribute values corresponding to a particular attribute; determining, based on a second machine learning model, an aggregated attribute value based on the plurality of attribute values; updating, based on the aggregated attribute value, a data field of the episode; adding the episode to the patient profile, wherein the patient profile comprises a plurality of episodes associated with the patient.

An exemplary computer-implemented method for generating and serving healthcare episodes and longitudinal profiles of healthcare episodes for patients and providers, comprises: receiving a plurality of care records; identifying, based on a first knowledge graph and a first set of machine learning models, groups of care records that should be merged into single episodes of care, wherein each episode is a predefined data representation comprising a predefined collection of data fields; creating, based on a second knowledge graph and a second set of machine learning models, individual episodes of care wherein each episode of care is populated based on the plurality of care records that comprise the episode; detecting, based on a third knowledge graph and a third set of machine learning models, data fields affected by data quality issues in one or more episodes; updating, based on a fourth knowledge graph and a fourth set of machine learning models, data fields affected by data quality issues in one or more episodes; augmenting, based on a fifth knowledge graph and a fifth set of machine learning models, data fields in one or more episodes; adding the episodes to patient profiles, wherein each patient profile comprises a plurality of episodes associated with the patient; adding the episodes to provider profiles, wherein each provider profile comprises a plurality of episodes associated with the provider; providing the healthcare episodes and longitudinal profiles of healthcare episodes for patients and providers through interfaces to users or causing a set of actions to be executed based on the healthcare episodes and longitudinal profiles of healthcare episodes for patients and providers.

In some embodiments, the first knowledge graph is based on a rules engine that identifies whether or not an input group of care records should be merged into a single episode of care.

In some embodiments, the first set of machine learning models is trained using a first training dataset comprising, a plurality of training samples pertaining to one or more patients, wherein each sample comprises, a plurality of care records, and; a label indicating whether or not the plurality of care records should be merged into a single episode of care.

In some embodiments, a featurizer module is used to process training instances for use in the first machine learning model.

In some embodiments, the featurizer module is used to process a plurality of care records, episode of care, or some combination thereof to create a feature vector based on the medical, demographic, socio-economic, clinical, geographic, administrative, financial and any other attributes contained in the input.

In some embodiments, the method further comprises: a classification model wherein for an input plurality of care records, episodes of care, or some combination thereof, the model predicts whether or not the input should be merged into a single episode of care.

In some embodiments, the method further comprises: a clustering-based machine learning model wherein an input plurality of care records are grouped (i.e., split into individual clusters) into multiple episodes of care, wherein each episode of care comprises a plurality of care records.

In some embodiments, the method further comprises: obtaining a label corresponding to a group of care records (i.e., a training/testing instance where the label indicates whether or not the group of care records should be merged into a single episode of care) by querying an expert user or oracle using an active learning framework.

In some embodiments, the second knowledge graph comprises a set of rules that denote the value for each attribute in an episode of care given the constituent care records that were merged into the episode (identified using the method(s) in claims 2, 6-8).

In some embodiments, the second set of machine learning models is trained using a second training dataset comprising a plurality of training samples, where each sample contains, a group of care records that constitute a single episode of care, and the value of each attribute in the resulting episode of care.

In some embodiments, the method further comprises: individual machine learning models for each attribute in an episode of care wherein; given an input plurality of care records that comprise the episode of care, each model predicts the value of a single attribute in the episode of care.

In some embodiments, individual machine learning models corresponding to different attributes may be trained jointly in a shared structure learning framework.

In some embodiments, the method further comprises: obtaining the value(s) for one or more attributes in one or more episodes of care by querying a user using an active learning framework.

In some embodiments, the third knowledge graph comprises a set of rules that determine for an episode of care, or one or more attributes within the episode of care, the degree to which it is affected by data quality issues or noise.

In some embodiments, the fourth knowledge graph comprises a set of rules that determine for an episode of care, or one or more attributes within the episode of care, how to replace, update or discard attributes that are noisy or affected by data quality issues.

In some embodiments, the third machine learning model is trained using a third training dataset comprising a plurality of training samples, where each sample contains, an episode of care, a binary value or probability indicating data quality issues or noise in the episode of care in its entirety or in one or more attributes in the episode.

In some embodiments, the method further comprises: a plurality of machine learning models, both for an episode of care in its entirety as well as for each attribute in the episode of care, wherein each model detects any data quality issues or noise in the attribute or in the episode of care.

In some embodiments, individual machine learning models corresponding to different attributes may be trained jointly in a shared structure learning framework.

In some embodiments, the method further comprises: detecting noise in episodes of care or their attributes by querying a user using an active learning framework.

In some embodiments, the method further comprises: a fourth machine learning model that is trained using a fourth training dataset comprising a plurality of training samples, where each sample contains, an episode of care, one or more values that should be used to update one or more attributes affected by noise in the episode of care.

In some embodiments, the method further comprises: a plurality of machine learning models for each attribute in the episode of care, wherein each model predicts a replacement value for attributes that are affected by noise.

In some embodiments, individual machine learning models corresponding to different attributes may be trained jointly in a shared structure learning framework.

In some embodiments, the method further comprises: detecting noise in episodes of care or their attributes by querying a user using an active learning framework.

In some embodiments, the fifth knowledge graph is based on a rules engine that derives high-level metadata for episodes of care.

In some embodiments, the method further comprises: a fifth machine learning model that is trained using a fifth training dataset comprising a plurality of training samples, where each sample contains, an episode of care, one or more values of high-level metadata that are relevant to the episode of care.

In some embodiments, episodes of care are updated with additional metadata.

In some embodiments, the method further comprises: creating patient profiles that are populated with a plurality of episodes of care, and; additional metadata related to the patients and their episodes of care.

In some embodiments, the method further comprises: creating provider profiles that are populated with a plurality of episodes of care, and; additional metadata related to the providers and their episodes of care.

In some embodiments, the method further comprises: creating visualizations of patient and provider profiles, their episodes of care, and additional metadata derived using expert knowledge, machine learning models, or combinations thereof.

An exemplary electronic device comprises: a display; one or more processors; a memory; and one or more programs, wherein the one or more programs are stored in the memory and configured to be executed by the one or more processors, the one or more programs including instructions for: receiving a plurality of care records; identifying, based on a first knowledge graph and a first set of machine learning models, groups of care records that should be merged into single episodes of care, wherein each episode is a predefined data representation comprising a predefined collection of data fields; creating, based on a second knowledge graph and a second set of machine learning models, individual episodes of care wherein each episode of care is populated based on the plurality of care records that comprise the episode; detecting, based on a third knowledge graph and a third set of machine learning models, data fields affected by data quality issues in one or more episodes; updating, based on a fourth knowledge graph and a fourth set of machine learning models, data fields affected by data quality issues in one or more episodes; augmenting, based on a fifth knowledge graph and a fifth set of machine learning models, data fields in one or more episodes; adding the episodes to patient profiles, wherein each patient profile comprises a plurality of episodes associated with the patient; adding the episodes to provider profiles, wherein each provider profile comprises a plurality of episodes associated with the provider; providing the healthcare episodes and longitudinal profiles of healthcare episodes for patients and providers through interfaces to users or causing a set of actions to be executed based on the healthcare episodes and longitudinal profiles of healthcare episodes for patients and providers.

An exemplary non-transitory computer-readable storage medium stores one or more programs, the one or more programs comprising instructions, which when executed by one or more processors of an electronic device having a display, cause the electronic device to: receive a plurality of care records; identify, based on a first knowledge graph and a first set of machine learning models, groups of care records that should be merged into single episodes of care, wherein each episode is a predefined data representation comprising a predefined collection of data fields; create, based on a second knowledge graph and a second set of machine learning models, individual episodes of care wherein each episode of care is populated based on the plurality of care records that comprise the episode; detect, based on a third knowledge graph and a third set of machine learning models, data fields affected by data quality issues in one or more episodes; update, based on a fourth knowledge graph and a fourth set of machine learning models, data fields affected by data quality issues in one or more episodes; augment, based on a fifth knowledge graph and a fifth set of machine learning models, data fields in one or more episodes; add the episodes to patient profiles, wherein each patient profile comprises a plurality of episodes associated with the patient; add the episodes to provider profiles, wherein each provider profile comprises a plurality of episodes associated with the provider; provide the healthcare episodes and longitudinal profiles of healthcare episodes for patients and providers through interfaces to users or causing a set of actions to be executed based on the healthcare episodes and longitudinal profiles of healthcare episodes for patients and providers.

DESCRIPTION OF THE FIGURES

The patent or application file contains at least one drawing executed in color. Copies of this patent or patent application publication with color drawing(s) will be provided by the Office upon request and payment of the necessary fee.

For a better understanding of the various described embodiments, reference should be made to the Description of Embodiments below, in conjunction with the following drawings in which like reference numerals refer to corresponding parts throughout the figures.

FIG. 3A illustrates exemplary augmented care records, in accordance with some embodiments.

FIG. 3C illustrates exemplary noise/error probabilities of episodes of care, in accordance with some embodiments.

FIG. 5A illustrates determining when to merge records using supervised learning, in accordance with some embodiments.

FIG. 5B illustrates determining when to merge records using supervised learning, in accordance with some embodiments.

FIG. 5C illustrates featuring a plurality of care records, episodes of care, or some combination thereof into a single feature vector, in accordance with some embodiments.

FIG. 6 illustrates determining how to merge records using machine learning, in accordance with some embodiments.

FIG. 8A illustrates a member view user interface with filtered attributes, in accordance with some embodiments.

FIG. 9 illustrates visualization of raw care records, in accordance with some embodiments.

FIG. 10 illustrates visualization of raw care records with optional filters, in accordance with some embodiments.

FIG. 11 illustrates an exemplary process for generating an episode of care using machine-learning techniques, in accordance with some embodiments.

DETAILED DESCRIPTION

Figure 1:
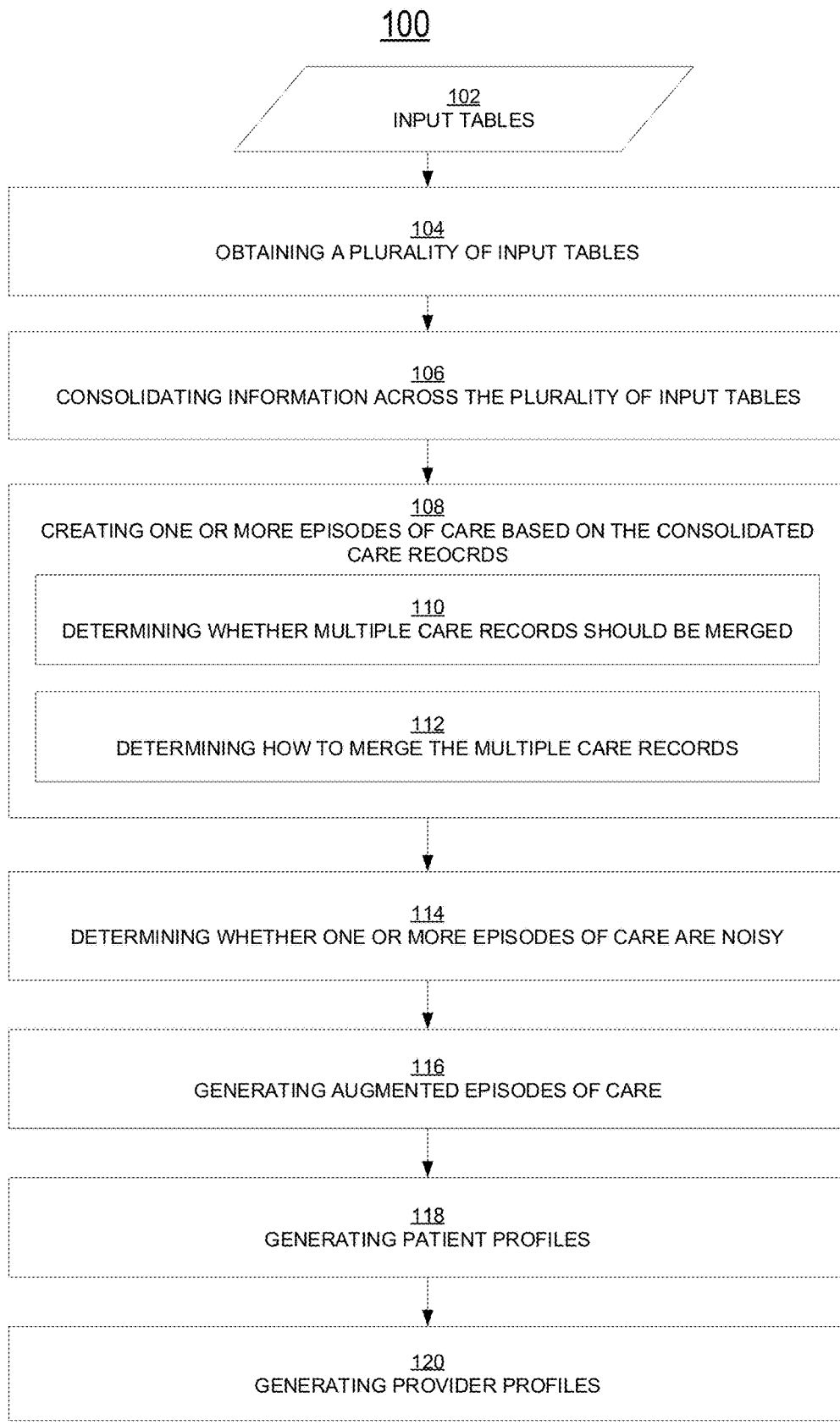
FIG. 1 illustrates an exemplary process for generating high-level healthcare data representations, in accordance with some embodiments.

The present disclosure includes systems, electronic devices, methods, non-transitory storage media, and apparatuses for generating and using high-level healthcare data representations (e.g., patient profiles, healthcare provider profiles and their episodes of care) using techniques such as machine learning algorithms. Embodiments of the present disclosure present significant technical improvements and numerous practical applications as described herein.

Embodiments of the present disclosure include an intelligent healthcare data fabric system that generates standardized high-level data representations for patients and providers that expose a complete longitudinal view of all episodes of care associated with them. These representations are derived from raw healthcare records using artificial intelligence and machine learning algorithms and are easier to interpret and analyze compared to raw care records. Furthermore, these representations of episodes of care are space-efficient, agnostic to coding formats/representations across payers and providers, address noise and other quality issues, are enriched and augmented with additional information, and support efficient serialization and deserialization operations, which in turn supports efficient storage and I/O operations. These data representations also separate the visualization and analysis of data, which can now be done against the episodes of care (rather than raw care records), that are processed using established best practices to deal with the complexity of the raw healthcare data.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Raw healthcare data contains a wealth of information regarding patients and healthcare providers (e.g., individual physicians, institutions, networks). However, raw healthcare data is often fragmented, noisy, and biased, and needs to be consolidated, standardized and contextualized in order to meaningfully analyze them (e.g., to understand the overall health profile of a patient or provider, to gain a longitudinal view of a patient or provider). There are a number of challenges associated with the integration of these fragmented, noisy raw healthcare data into a data fabric, as discussed below.

Computational and Algorithmic Complexity of Joins

Raw healthcare data is typically stored (and made available) in fragmented form. For example, the raw data might be split into different tables on the basis of time (separate tables for records in a given month or year), type of service (separate tables for inpatient vs outpatient records), setting of service (separate tables for inpatient hospital, outpatient hospital, clinic, skilled nursing, pharmacy, laboratory, professional, etc. records), or a combination thereof.

Even within the same table, there may be multiple care records for a patient that should be consolidated. Furthermore, analyzing healthcare data often requires the use of additional metadata, for example, about providers (e.g., details about their practice locations, specialties and services offered, sanctions, etc.) and patients (e.g., their enrollment details, demographic information, etc.). These metadata are typically also stored in other tables.

A complete health profile for a patient or provider therefore often depends on relating information across some or all of the available data and metadata tables. Thus, analysis pipelines that depend on the complete view of a patient or provider's history must first join and consolidate information in all the healthcare data and metadata fragmented across multiple tables. Depending on the number and size of the tables that must be combined, these join operations can be computationally expensive, algorithmically complex, and serve as a bottleneck in the analysis of these data.

For example, consider answering the following question: "total spending on all patients enrolled under plan 'X' over the age of 65 that saw a cardiologist in December 2017 and were eventually admitted to a hospital to receive inpatient care within three months of their visit and must be signed up for home delivery of medications from a pharmacy within 10 miles of where they live." Answering this kind of question requires the consolidation of information from many clinical and claims tables for both clinic visits to specialists as well as inpatient hospitalizations across multiple years as well as tables containing metadata about patients (e.g., their enrollment information and demographics).

Determining Whether to Merge Records

Over the course of a single episode of care for a patient, multiple data records may be generated. An episode of care refers to a data structure representation of distinct interactions or events in the patient's medical history to treat or diagnose a medical condition, comprising one or more raw care records. The episodes can include outpatient visits (e.g., in-person, remote), hospitalization, emergency room visits, skilled nursing facility or long term care, diagnoses, services performed (e.g., lab tests, medical and surgical procedures), home health visits, reimbursement/charges, providers involved, etc.

For example, an inpatient hospital stay that lasts 30 days might be split into multiple care records as follows,
  Records collected on a weekly basis by the hospital relating to bed utilization, transfers through the hospital, etc.,
  Records for services provided by professionals involved in the hospital stay such as doctors, nurses, etc., where each of the providers might submit individual records,
  Records for drugs, prostheses, etc.

Analyses based on such episodes of care (e.g., average cost of inpatient hospitalizations, etc.) must therefore aggregate or merge these raw records into more naturally interpretable "episodes of care". However, this process is challenging.

While records that appear close together in time (or overlap each other in time) may be part of the same episode of care, they may just as easily also be part of different episodes of care. For example, records submitted back to back may belong to a single episode of care (e.g., an overnight ED visit leading to a hospitalization) or be part of different episodes of care (e.g., an ED visit resulting in a home discharge following by a next-day recurrence and hospitalization). Scenarios such as this complicate the decision for whether or not the records should be merged together into a single episode of care.

Determining How to Merge Records

Even after identifying which raw care records should be merged into the same episode of care for a patient, the actual process of consolidating conflicting information across these care records is challenging. For example, attributes such as the principal diagnosis for the episode, the discharge destination after the episode of care, the primary rendering or attending physician involved in the episode of care, among others, are harder to consolidate due to potential inconsistencies between the care records or due to the subjectivity involved in merging them.

Similarly, records can often be duplicated, revised, rejected; these variations and inconsistencies must be resolved when creating an overall picture of an episode.

Attributing Services to Providers

Identifying providers that were primarily responsible for providing services is non-trivial for episodes that engage many providers. In particular, determining the provider that was primarily responsible for an episode from among multiple providers listed on a medical service record is often challenging. This issue is further exacerbated when merging records, where multiple primary provider(s) responsible for a single episode of care might be listed in one or more (but not all) of the constituent raw care records in the episode.

Identifying the Setting for Service Provided

Similar to the provider attribution issue, identifying the setting and type (i.e., inpatient vs outpatient) of service for an episode of care is a non-trivial problem.

Healthcare data records such as claims typically have attributes such as facility type or place of services (hospital/nursing home/ambulatory center, etc.) and revenue codes that offer useful information of value for inferring the setting and type of service provided. However, these inferences might be complicated by inconsistencies or noise in these different sources of data. In addition, cases like outpatient observation visits where patients had access to a bed over multiple days, or patients admitted for inpatient care who left early, can complicate this problem (especially as these cases are difficult to distinguish from noise). Furthermore, the type and setting of the service for an episode of care may only be clear in the context of all constituent records involved.

Identifying Noise and Errors in Records

Healthcare data records often contain inconsistent or noisy data that stem from a variety of sources. Human error is one such example, which manifests as incorrect/noisy data in healthcare data records. For example, consider a patient transferring from Hospital A to Hospital B with a record submitted by each hospital. Ideally, the discharge destination for Record A as well as the source of admission for Record B would be "Hospital Transfer", but this may not necessarily be the case; as one or both of the facilities may forget to document the transfer accurately (or, more commonly, as providers might only complete a small subset of fields and the additional fields may have their values defaulted). Further challenges result from issues such as duplicate records being submitted, multiple records being submitted for adjustments or updates with the original record not being withdrawn, etc. Another commonly observed confounding example is records with noise and blanks, such as claims for services provided in the emergency department (ED) appearing without the type of admission being set as "Emergent".

Augmenting Records with Additional Metadata

Healthcare data contain a wealth of information about the particular service being delivered. For example, these records may include ICD codes detailing the diagnoses and procedures in the episodes, identifiers for providers involved in the care, place and type of service codes, payment information, etc. However, any analyses that depend on a high-level health profile of patients must first perform additional processing on these raw records to obtain a more complete and expanded understanding of these additional entities. For example, for ICD codes, they must be mapped to an understanding of what these codes are and what their clinical significance is. More generally, raw records data need to be augmented with additional metadata about diagnoses, procedures, providers, demographics, etc. through what is often a computationally intensive and cumbersome process.

Reconciling Variations in Coding Formats Across Payers and Providers

Another potential source of noise in healthcare data is the mapping of attributes in records using multiple potential data dictionaries as these records make their way through various provider and payer platforms and systems. For example, a single organization that processes records from multiple provider systems might receive records from each of these providers with different provider identifiers. Thus, providers can be identified using National Primary Provider Identifiers (NPIs), Medicare IDs. Tax Identifiers (TINs), Primary Provider, Enrollment, Chain and Ownership System Identifiers (PECOS), or other payer specific identifiers, among others. Mapping provider identifiers across these different systems can introduce noise in the data due to the mappings potentially being incomplete or inconsistent (and in most cases there being the potential for many to many mappings). Similar issues might occur when mapping other attributes that might be coded using different dictionaries. Source of admission codes, discharge destination codes, service or setting type codes, provider specialties, etc. are examples of such attributes that might be coded with varying degrees of granularity and/or containing different allowed values across various data dictionaries.

Embodiments of the present disclosure include a healthcare data fabric system that processes raw healthcare data to generate standardized, high-level healthcare data representations. The system can address various challenges of processing raw healthcare data, including data organization, complexity, noise, merging, attribution, standardization, tagging/categorization, augmentation. The resulting data representation supports a broad range of computational analyses and visualizations.

Embodiments of the present disclosure can ingest care records expressed in various formats using a broad group of data dictionaries and generate data representations of episodes of care that are uniform across these formats. The resulting data representations (e.g., patient profiles, provider profiles and the episodes of care associated with them) are readily interpretable and easier to analyze in terms of algorithmic complexity and computational resources. The data representations are enriched with additional metadata about the patients, providers, payers, episodes, etc. that support downstream high-level analyses. The system identifies and addresses noise, errors, and/or biases in the data.

The high-level representations are made available to end users, who are abstracted from the processing of the raw healthcare data records and are able to visualize and analyze data in a standardized format.

The high-level representations produced support easy serialization and deserialization for storage while also being lightweight.

FIG. 1 illustrates an exemplary process for generating high-level healthcare data representations, in accordance with some embodiments. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

At block 104, an exemplary intelligent healthcare data fabric system (e.g., one or more electronic devices) receives a plurality of input tables 102. The input tables 102 can include care records, provider metadata, patient metadata, and prior knowledge, or any combination thereof.

Figure 2:
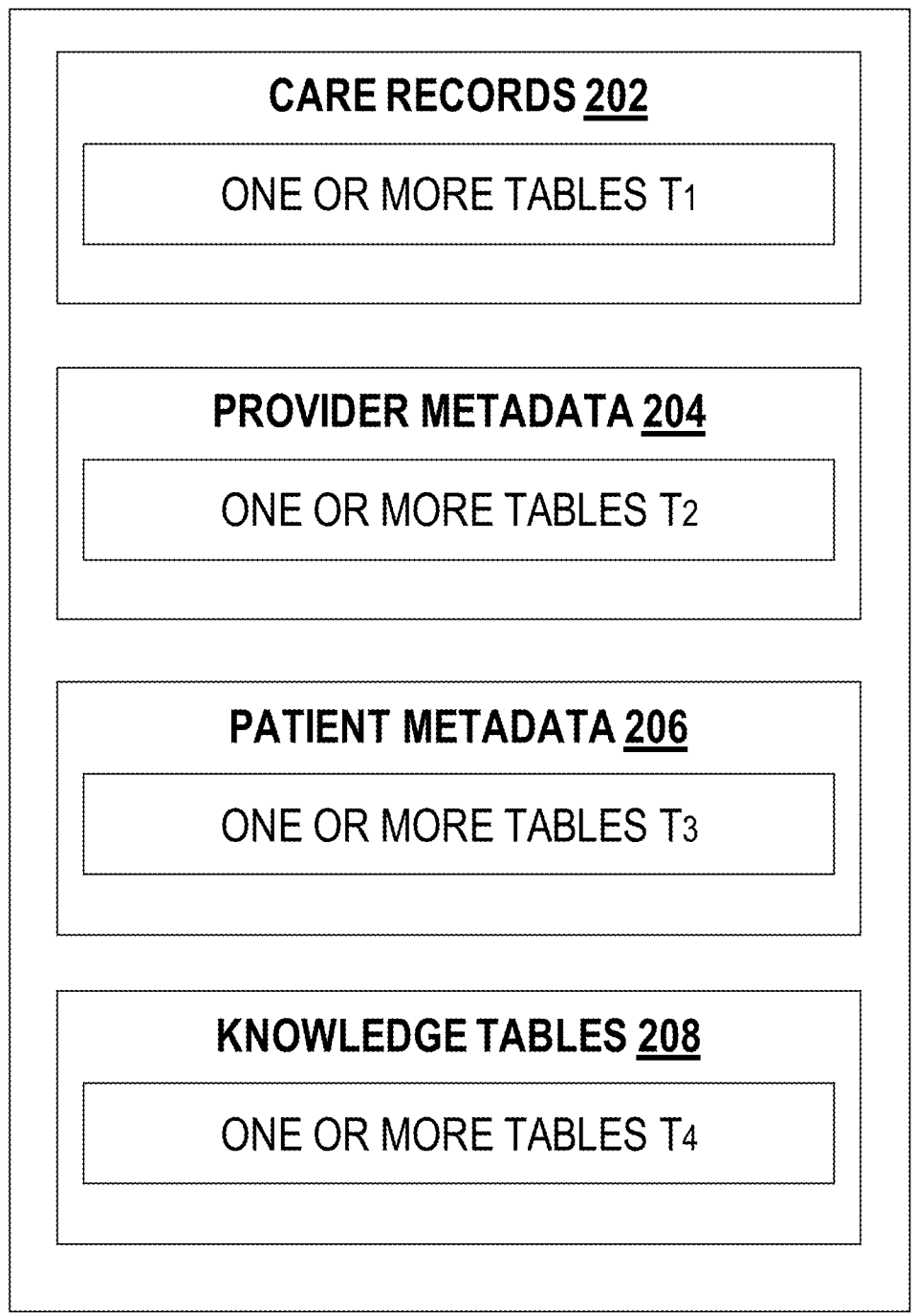
FIG. 2 illustrates an exemplary collection of input tables, in accordance with some embodiments.

FIG. 2 depicts an exemplary collection of input tables, in accordance with some embodiments. With reference to FIG. 2, the input tables can include care records 202. Each care record can include care record attributes, such as medical claims data, clinical (EHR) data, wearable data, self-reported patient data, omics data, imaging data, social determinants of health data, demographic data, administrative data, economic data, or any combination thereof. For example, care records 202 can include information such as patient attributes (e.g., age, demographics, etc.), provider attributes (e.g., practice information, specialties, etc.), diagnoses and prognoses made during the care delivery, information about which diagnoses were pre-existing, procedures performed during the care delivery, details about the care delivery, results from diagnostic/therapeutic tests and procedures, or any combination thereof. Details about the care delivery can include the setting of service (e.g., inpatient vs outpatient), place of service (e.g., hospital vs office, etc.), type of admission, source of referral, discharge disposition, or any combination thereof.

The care records 202 can include one or more tables $T_1$. For example, $T_1$ can be a plurality of tables corresponding to different time periods, different types of service, different types of provider, different lines of business, different platforms, or any combination thereof.

The input tables can include provider metadata 204. The provider metadata 204 can include attributes of a plurality of providers, such as information about provider specialization, capacity, insurance plans accepted, practice information and locations, demographics, ratings and rankings, etc. The provider metadata 204 can include one or more tables $T_2$.

The input tables can include patient metadata 206. The patient metadata 206 can include attributes of a plurality of patients, such as their insurance plan, demographics, social determinants of health, preferred care locations, etc. The patient metadata 206 can include one or more tables $T_3$.

The input tables can include knowledge tables 208. The knowledge tables 208 can include prior knowledge such as medical knowledge (e.g., ICD code definitions, information about common surgeries, etc.). The knowledge tables 208 can include one or more tables $T_4$.

The input tables are not limited to an arrangement of data in rows and columns and can include other arrangements of data such as knowledge graphs.

It should be appreciated that the input tables depicted in FIG. 2 are merely exemplary. The input tables can further include additional tables with other relevant healthcare data that can augment and/or complement the above-described data.

At block 106, the system consolidates information across the input tables. In some embodiments, the system augments the care data records (e.g., care records 202) with information about providers (e.g., from provider metadata 204), patients (e.g., from patient metadata 206), medical knowledge (e.g., from knowledge tables 208), clinical data and any other additional relevant information.

FIG. 3A illustrates an exemplary output (i.e., augmented care records) of block 106. As depicted, each care record includes record attributes, attributes of the provider associated with the care record, and attributes of the patient associated with the care record. Thus, the output of block 106 is an augmented version of the care records (e.g., care records 202) in which each care record is associated with or linked to metadata of the corresponding patient, corresponding provider, and/or other relevant information (e.g., medical codes, clinical actions). Accordingly, block 106 sets up associations between the records themselves and between records and metadata/knowledge such that all information is linked and organized together for use.

The consolidated care records can be relatively large (e.g., several TB of storage space). In some embodiments, the system uses parallelization and distributed storage/processing to process and store the consolidated care records. In some embodiments, compression, hashing, de-duplication can be used to efficiently handle and process these data in a space and memory efficient manner.

At block 108, the system creates one or more episodes of care based on the augmented care records. In some embodiments, the system organizes, groups, and/or merges the consolidated care records into episodes of care. An episode of care refers to a data structure representation encompassing distinct care records in the patient's medical history to treat or diagnose a set of one or more medical conditions. An episode of care may correspond to a contiguous, continuous or recurring set of services provided by a common set of providers in relation to treating or diagnosing this set of one or more medical conditions. The data representation for an episode of care contains a plurality of predefined data fields. Each data field can be associated with a predefined format, a predefined unit, and/or a combination thereof. For example, an episode might include information about the patients and providers involved, the services provided (including diagnoses and procedures made, the settings where care was delivered, drugs and equipment dispensed or prescribed), other healthcare information such as tests, notes, outcomes of the care, charges and reimbursed amounts, co-pays, etc. among others.

In one exemplary episode, a patient may visit an emergency room for a set of one or more medical conditions, which results in an overnight admission, a 7-day hospital stay, an operation, an infection from the operation, an admission to the ICU, and an eventual discharge. While multiple care records may be generated by different healthcare providers for the events above, these events all relate to one continuous episode of care.

In another exemplary episode, a patient may visit a clinic twice weekly for 20 weeks for physical rehabilitation. While multiple care records may be generated for the multiple visits, these events all relate to one continuous episode of care.

Accordingly, each episode can include outpatient visits (e.g., in-person, remote), hospitalization, emergency room visits, skilled nursing facility or long term care, diagnoses, services performed (e.g., lab tests, medical and surgical procedures), home health visits, reimbursement/charges, providers involved, etc., or any combination thereof.

Figure 3B:
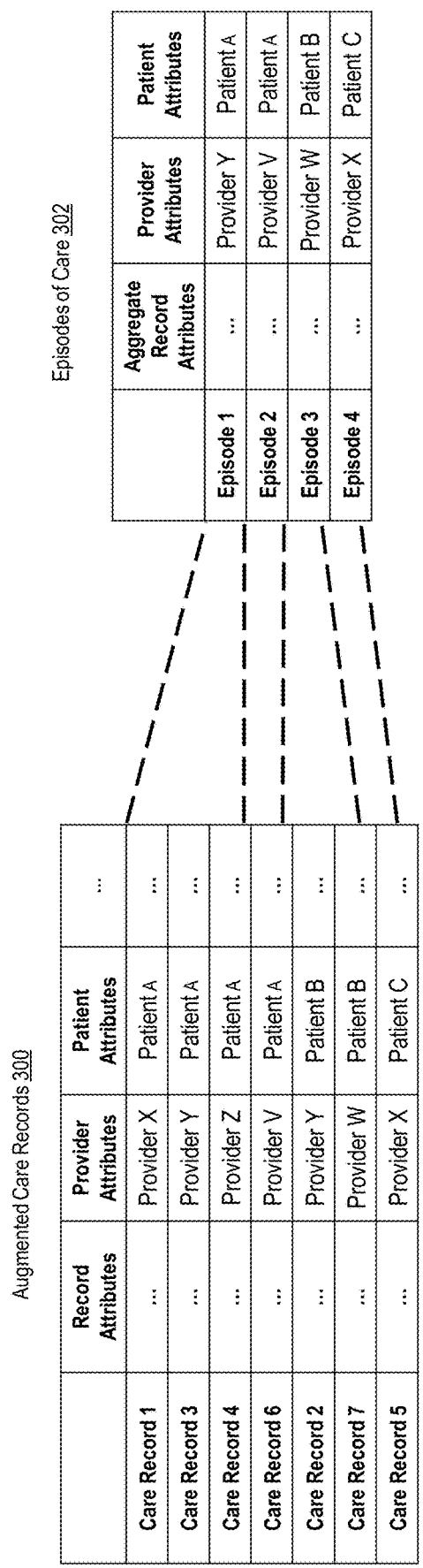
FIG. 3B illustrates exemplary episodes of care, in accordance with some embodiments.
Figure 3D:
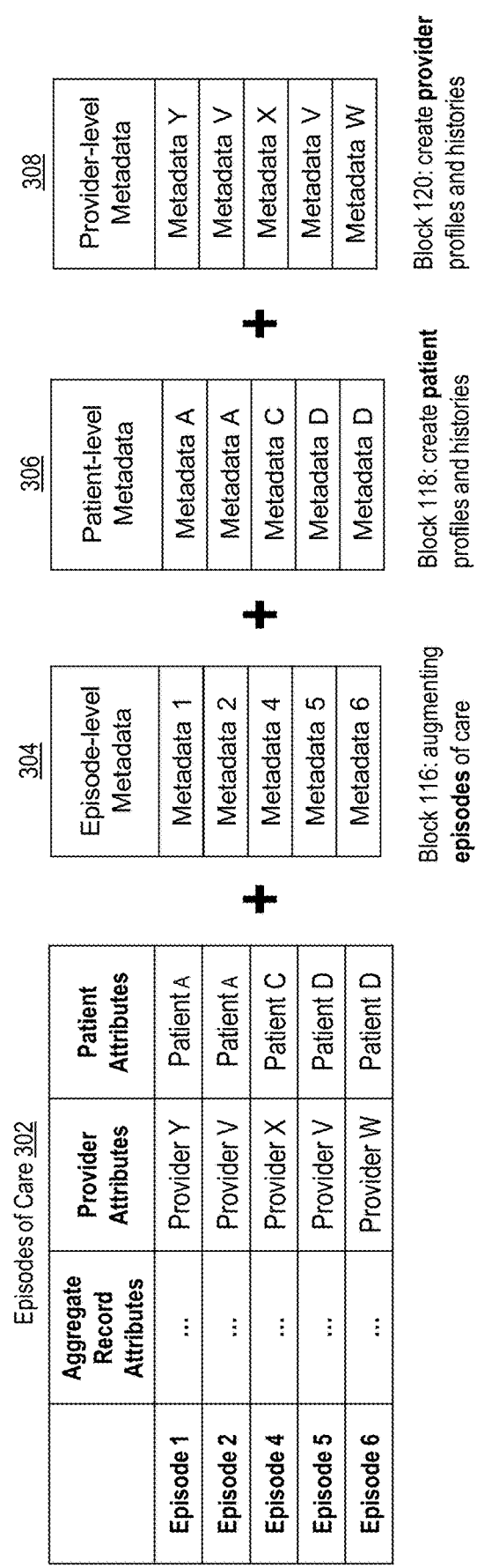
FIG. 3D illustrates exemplary augmented episodes of care, in accordance with some embodiments.

FIG. 3B illustrates a plurality of episodes of care 302 created based on the augmented care records 300, in accordance with some embodiments. As depicted, Care Records 1, 3, and 4 are merged into Episode 1 (Primary Provider Y, Patient A); Care Records 6 is not merged with any other care records and becomes Episode 2 (Primary Provider V, Patient A); Care Records 2 and 7 are merged into Episode 3 (Primary Provider W, Patient B); Care Records 5 is not merged with any other care records and becomes Episode 4 (Primary Provider X, Patient C).

With reference to FIG. 1, the block 108 further includes block 110 (identifying whether to merge multiple records into a single record of care) and block 112 (identifying how to merge attributes across multiple records of care).

At block 110, the system constructs episodes of care; a plurality of raw care records (one or more) are grouped into episodes of care for a single member. The grouping of care records into episodes can be made based on machine learning techniques, expert-defined rules, or a combination thereof.

In some embodiments, a knowledge graph based on expert-defined rules may be used to group raw care records into episodes. The knowledge graph can include specific rules developed via a combination of medical domain knowledge and empirical data. As an exemplary example, all care records for a member with overlapping service dates at the same facility may be grouped under a single episode of care. The actual knowledge graph may rely on various attributes in the care records such as service dates, patient vitals and clinical states, providers involved in the care, prognoses, diagnoses, procedures and medications, payment information, etc.

In some embodiments, a machine learning system may be used to intelligently group care records into episodes of care. Thus, for a single member, the system receives a plurality of raw care records and produces a number of episodes of care where each episode of care comprises one or more care record(s). FIGS. 5A and 5B present two such examples where machine learning methods are used to identify which raw care records should be grouped into high-level episodes of care. Both embodiments depend on a featurizer module defined between care records, episodes of care or some combination thereof (FIG. 5C).

As shown in FIG. 5C, an input plurality of (a) care records or (b) episodes of care or (c) combination of care records and episodes of care may be processed through a featurizer module (say f(a, b, . . . , n)) to derive a single d-dimensional feature vector that describes the entities (i.e., raw care records and/or high-level episodes of care) in the input. Thus, given a variable number of entities as input (between 1 to n), the featurizer module derives features for each constituent record or episode of care to finally generate a single, d-dimensional feature vector.

For care records or episodes, both snapshot features (that depend only individual records or episodes) and longitudinal features (that depend on multiple records/episodes) may be derived.

Some examples of snapshot features are,

Features related to providers such as their specialties (hospitals, nursing homes, cardiologists, family medicine, etc.), the payment amount attributed to each provider (or a higher level construct such as provider type, specialty, etc.), the geographical locations of the providers involved in the episode (providers' zip codes used as categorical features, etc.), etc. These features may be used as indicator values (i.e., 0 or 1) when categorical (e.g., provider specialties, etc.) or as continuous values (e.g., payment amounts to cardiologists, payment amounts to hospitals, etc.).

Features related to diagnoses and procedures, either in the form of raw codes or as higher level groups related to the diagnoses and procedures, used as one-hot encoded/indicator vectors for each categorical feature.

Features related to the patient's clinical/physiological state, such as their vitals, metabolic state, etc. These features may be categorical (blood pressure as low/medium/high, etc.) or continuous (heart rate in BPM, etc.).

Similarly, examples of longitudinal features are,

The number of days of overlap with other care records or episodes in the input record/episode's temporal vicinity. In some embodiments, the number of days of overlap between records/episodes can be negative (i.e., one episode starts after another ends) or can be capped to a minimum value of zero.

Other time-dependent features based on various attributes might measure recency or frequency of various events of interest (e.g., time since last cardiologist visit, frequency of inpatient hospitalizations over the last 180 days, etc.).

Given features derived for a plurality of raw care records and/or episodes of care, the featurizer module combines these features into a single, consolidated feature vector (that represents all the constituent care records and episodes in the input). This may be done by, Numerically aggregating up to 'n' feature vectors (where each feature vector is derived for a care record or episode). To aggregate categorical features encoded as indicator variables, the values across individual feature vectors (for a single categorical feature) may be added and further processed through a function such as mean, mode, binary step, etc. or by calculating a 'bag of words' vector that uses either an indicator variable or a count for each category. For a single continuous feature, the collection of values across all individual feature vectors may be used to create several summary features such as the min, max, mean, median, mode, quartile values, etc for use as features representing the aggregate feature vector.

In some embodiments, features may be derived for a pair of entities, where each entity is either a raw care record or episode of care. Then, the aggregate feature vector for the input pair may be a concatenation of the two constituent feature vectors.

In some embodiments, additional processing may be performed on a collection of feature vectors using techniques that are robust to a variable number of inputs (e.g., dynamic time warping, sparse autoencoders with a zero-padded input, etc.) to generate a post-processed feature vector.

In different embodiments, the features defined above may be defined similarly for either raw care records or for episodes of care that themselves comprise one or more care records, as necessary. Thus, when deriving features for an episode of care comprising multiple raw care records, the features may be derived (a) using the attributes available in the high-level episode of care or (b) individually for each raw care record, and combined using the methods described above.

In FIG. 5A, an embodiment of the system to group care records into episodes of care using machine learning is shown. Using a bottom-up approach, features are derived (using techniques listed above) for consecutive (in terms of service dates or time stamps) care records and/or episodes of care and are input into a supervised machine learning model M that determines whether or not the input entities (that may be a combination of care records and/or episodes of care) should be grouped into a single episode of care. For example, a feature vector derived from records A and B is input into the model to determine if they should be grouped into a single episode; a feature vector derived from records C and D is input into the model to determine if they should be grouped into a single episode; a feature vector derived from records E and F is input into the model to determine if they should be grouped into a single episode, etc.

After the first iteration, the system repeats the process for the current list of care records/episodes. For example, a feature vector derived from episode AB and episode CD is input into the model to determine if they should be grouped into a single episode; a feature vector derived from record F and episode GH is input into the model to determine if they should be grouped into a single episode, etc.

The process is repeated iteratively until all remaining consecutive pairs of care records/episodes of care should not be merged together as determined by the model. At this point, any remaining ungrouped care records are converted to episodes of care (containing only a single care record). Thus, in the first iteration of this bottom-up approach, only pairs of raw care records are passed as input to the model M; however, subsequent iterations may use the model to evaluate whether or not episodes of care created in a previous iteration should be merged with other care records or episodes of care.

In FIG. 5B, another embodiment of the system that groups claims into episodes using machine learning is shown. The steps are, First, a pair-wise similarity metric is calculated between every pair of raw care records to generate a kernel matrix. The features described above are generated for each raw care record, following which the feature vectors for pairs of records are used to calculate a similarity score. In some embodiments, a supervised machine learning model similar to M may be used to derive the similarity score. In other embodiments, the similarity score may be unsupervised (e.g. L-p norm of the difference between the feature vectors, arbitrarily high dimensional dot products between the feature vectors, etc).

A hierarchical agglomerative clustering approach (either bottom-up or top-down) may then be used to identify clusters of care records given the kernel matrix, wherein the raw care records within each cluster constitute a single episode of care. The clustering may be implemented with user-defined thresholds that require a minimum similarity score between records in an episode of care to control the number of clusters discovered, or these thresholds may be learned during training as hyperparameters.

Furthermore, missingness in features (under various assumptions of missingness such as MCAR, MAR, MNAR, etc.) may be handled using various methods, such as imputation (based on mean, zero, last seen value for longitudinal values, etc. among other imputation methods), using an additional 'missing' category for categorical features, etc. Other methods such as multiple-imputation, or parametric imputation models (such as EM, etc.) may also be used in some embodiments. In some embodiments that use similarity/dissimilarity scores between records and episodes (e.g., as described under the "Computational and Algorithmic Complexity of Joins" Section or support-vector models), missingness in features may be handled directly by the kernel function by normalizing the dot product between feature vectors to account for missing features.

In some embodiments, the featurization of record/episode pairs or the creation of the kernel matrix for a given plurality of care records may be parallelized to improve performance.

In some embodiments, time-series based modeling approaches that depend on longitudinal data (i.e., data or features for multiple records that depend on temporal features) may be used to predict whether or not each new record that is streamed incrementally for a patient (i.e., when iterating over temporally sorted records consecutively) should be (a) merged into the currently 'open' episode of care or (b) should be used to create a new episode of care. In such an embodiment, episodes of care may be 'closed out' (i.e., no new care records shall be merged with them in the future) based on some threshold of d days (i.e., no two records may be merged together if they are >d days apart with no days of overlap, etc.), picked either as a hyperparameter or defined by the user.

The training of the model may involve splitting the data into training/validation sets using techniques such as k-fold/leave-one-out, past/future splits or random splits (as some examples) for hyperparameter training. Furthermore, the machine learning models may be trained to predict labels that are discrete (0/1 or −1/1), continuous (real-valued numbers), probabilistic (values between 0 and 1), multi-class (one of 'k' possible labels) or sequential (using models such as Markov models, LSTMs, etc.).

The model 404 can be trained using training data 402. The training data 402 includes a collection of samples (1, 2, 3, . . . , n) where each sample comprises a plurality of raw care records, episodes or both. For each of the training samples, a label is further included that indicates whether or not the care records and episodes in the sample should be merged together (label=1, positive training sample) or not merged together (label=0, negative training sample).

In some embodiments, the model 404 is a logistic regression model configured to receive features for a collection of training samples and provide an output 408 indicative of whether or not a featurized group of care records and/or episodes of care should be merged together into a single episode of care. The logistic regression model is trained based on the training data 402.

In some embodiments, the model 404 is a neural network model configured to receive inputs and produce outputs defined below. The neural network model is trained based on the training data 402. The neural network model can be either a snapshot model (DNN, feed-forward neural network, etc.) or a temporal model (e.g., RNN). It should be appreciated that other types of supervised classification models can be trained based on the training data 402 to determine whether a group of care records should be merged into a single episode of care. Some examples are, support vector machines (SVM), tree-based models (random forests, decision trees, etc.), perceptrons, discriminant analysis models (LDA, GDA, etc.), Naive Bayes, Markov-based models, etc.

After the model 404 is trained, the system can use the trained model to determine which of the care records (e.g., care records 1-7 in FIG. 3A) to merge.

In some embodiments, the system uses active learning frameworks. The system uses a set of initial labelled training data to train the model 404 and then incrementally requests labels for examples. In each round of active learning, the model 404 can assess informativeness of unlabeled data, select the most informative examples to be labelled by an oracle, and be retrained using the newly labelled data. The active learning frameworks can include membership query synthesis, pool-based sampling, stream-based sampling, to allow the model to query an oracle (i.e., an expert user) for labels (using strategies such as balanced exploration/exploitation, expected change/error, exponentiated exploration, sampling, querying by committee or subspaces, variance reduction, conformal predictors, mismatch-first farthest-traversal, etc.) for select examples that are deemed to be ambiguous. The active learning frameworks can be built using smaller amounts of carefully chosen, most informative examples that can be labeled in a scalable manner by human experts or other oracles.

In some embodiments, the oracle is requested to label unlabeled data, which is used to retrain the model. In some embodiments, the oracle is requested to label outputs of the model, which is used to retrain the model.

At block 112, the system determines how to merge a group of care records (i.e., a care records group that was determined to be merged in block 110) into a single episode of care.

To merge the multiple raw care records into a single episode of care, the system fills the predefined fields/attributes in the episode based on the data in the multiple care records. If none of the raw care records contain a value for a predefined attribute in the episode, the system can populate the value using machine learning models or mark the attribute as missing in the episode. Thus, the system shown in FIG. 6 (a) consolidates values for attributes that may exist in the individual raw care records (and additionally populates this value using predictive models if it's missing in one or more raw care records) into a single value for use in the episode of care and (b) determines the values of attributes that exist only in episodes of care (and not raw care records) using contextual information available in other attributes in the raw episodes of care.

For a given attribute in high-level episodes of care, if the constituent care records include inconsistent values for the attribute (i.e., the value is not the same in all constituent care records), the system decides how these inconsistent values should be consolidated into a single value in the episode of care. For example, with reference to FIG. 3B, the system can determine that, when merging Care Records 1, 3, and 4, the resulting episode will include Provider Y as the primary provider, even though the three care records list three different providers X, Y, and Z. Similarly, the system can determine that, when merging Care Records 2 and 7, the resulting episode will include Provider W as the primary provider, even though the two care records list two different providers Y and W.

The techniques used to consolidate attribute values across raw records of care into a single episode of care may also be straightforwardly extended to populate attribute values in an episode of care by combining (a) raw records of care with previously created episode(s) of care or (b) combining multiple episodes of care into a single episode of care. Thus, the input used to populate attribute values in a high-level episode of care may be derived from constituent raw care records, constituent episodes of care or some combination thereof.

In some embodiments, a knowledge graph may be used to populate attribute values in episodes of care if one or more of its constituent care records/episodes include the attribute values and they indicate no inconsistencies. For example, if the attribute being populated is the provider identifier and if all the constituent records of the episode of cares list the same provider identifier, it can be used as the "primary provider" for the episode. As another example, the total cost of care for an episode may be the sum of all costs incurred in its constituent records of care. As another example, if the multiple care records list different dates, the "start date" and the "end date" for the episode can be the first date and the last date across the records, respectively. When filling the fields of the episode of care, the system can convert the data from the multiple care records into predefined formats and/or units. For example, attributes like provider IDs can be converted into NPIs, units for height can be standardized (e.g., from feet/inches and metres/centimetres to feet/inches) etc.

In some embodiments, the system uses a knowledge graph to determine how to populate attributes in an episode of care by using potentially inconsistent data from its constituent records of care. The knowledge graph can include specific rules developed via a combination of medical domain knowledge and empirical data. For example, a primary provider for an episode of care can be selected from among a set of providers that appear in the care records based on the reimbursement amount, number of diagnoses and procedures, the nature/severity of the diagnoses and procedures, the previous association history of the provider with the patient, the nature of the diagnoses and procedures, the specialty and experience/seniority of the provider, and/or other information associated with the providers. An exemplary rule can dictate that the primary provider for an episode is the most expensive provider, the provider with the most history with the patient, or the provider with the most substantial procedure (e.g., based on a customized ranking of procedure severity) out of all providers associated with the care records to be merged, etc. Another rule can dictate the collection of providers to be the union of all providers across the records. Another rule can dictate the collection of ICDs (diagnoses and/or procedures) involved in an episode to be the union of all ICDs across the records.

In some embodiments, the system uses one or more machine learning models to populate an attribute in a high-level episode of care. FIG. 6 illustrates an exemplary machine learning model N for determining how to populate attributes in an episode of care based on multiple raw care records that comprise the episode of care.

The machine learning models can be used to predict the values for various attributes in an episode, using features derived from the constituent care records. When deriving features from a plurality of raw care records (where the exact number of constituent records in an episode may vary across episodes), the features may be combined using techniques described above. Some examples of attributes that may be populated using the model and the associated features useful for these predictions are, The principal diagnosis for an episode of care. Features relevant to this attribute might be derived from diagnosis codes filled in the constituent care records, as well as additional contextual information derived from the procedures performed, the providers involved in the care records, the length of stay for each care record, etc.

In some embodiments, the model might be trained to identify all possible diagnoses made during an episode of care. Based on the treatments prescribed (e.g. warfarin) or procedures performed (e.g. atrial ablation) one might infer any diagnoses likely to be made (e.g., atrial fibrillation).

The attending provider for an episode of care. Features similar to the previous examples may be used for such a model.

In various embodiments, various other attributes related to the episode's diagnoses, prognoses, medications, providers involved in the episode, patients' clinical and physiological state, etc. may be populated in episodes of care using features defined above and in earlier parts of this document.

In some embodiments, missing values in features for the machine learning models may be handled using techniques described herein.

In some embodiments, separate models might be trained to impute each attribute in an episode of care (shown in FIG. 6). In order embodiments, the machine learning models for different attributes may be trained in a shared structure learning framework using techniques like multi-task or transfer learning. For example, models to predict the primary attending provider and primary surgeon on an episode of care might benefit from being trained together, as these attributes are likely related and often relate to the same individual. Similarly, models that predict the medical attributes for a patient (such as vitals, diagnoses, etc.) would benefit from sharing information with models that predict which procedures were performed, which medications were prescribed, etc.

As depicted, the supervised learning model 414 is configured to receive an input group of care records (i.e., two or more care records) to be merged into a single episode and provide an output 418 indicative of the value of Attribute A. For example, with reference to the example in FIG. 3B, the model 414 can receive as input raw care records 1, 3, and 4 and provide an output indicative of the value of the primary provider in the high-level episode of care (i.e., Provider Y).

In some embodiments, this model training can be performed using the approach described herein. For example, the model might be trained using cross-validation techniques (such as k-fold, leave-k-out, temporal-splits, etc.) that split the data into training/validation sets for learning the optimal hyperparameters and other model selection tasks.

The model 414 can be trained using training data 412. The training data 412 includes a plurality of care records groups (1, 2, 3, . . . , m). A care records group is a group of two or more care records to be merged into a single episode. For each care records group, the training data includes features of the care records in the group.

For each care records group, the training data further includes a label indicating the value of a single Attribute A for the resulting episode of care. The label can be generated manually if not already present in the episode of care. The labels (and therefore the outcomes of interest to be populated in the episode of care) can be discrete/continuous/multi-class.

In some embodiments, the model 414 is a regression model used to predict attribute values that are continuous (e.g., blood pressure, length of stay, payment information, etc.). The exact model may be a linear regression, neural network, support vector regression, or any of the other possible regression models across various embodiments.

In some embodiments, the model 414 is a classification model used to predict attribute values that are binary (e.g., service type inpatient vs outpatient, whether or not the care was emergent, etc.). Various models such as logistic regression, deep/shallow neural networks (including specific classes of models such as CNNs, etc.), SVMs, k-nearest neighbours, GMMs, etc. may be used in different embodiments.

In some embodiments, the model 414 is a multi-class classification model used to predict attribute values that are categorical (e.g., the patient's discharge disposition as one of home, subsequent care, etc.). The model be multi-class models (e.g., softmax regression) or multiple one-vs-rest binary classification models. The exact model type may be any of the possibilities defined above.

In some embodiments, the model 414 is a supervised clustering-based approach that may be used to predict attribute values that are categorical. In particular, for a particular attribute (e.g., physician identifier), all records with the same value for the attribute may be grouped into clusters, thus resulting in a cluster for every possible categorical value of the attribute. Then, the attribute value in a novel record is assigned based on the cluster it's most similar to. The actual clustering method could be k-means/medoids, k-nearest neighbours, GMMs, etc. The similarity metric used to compare novel records to cluster may be distance based (e.g., Euclidean distance), functional (e.g., similarity defined using medical attributes such as diagnoses, procedures, etc.) or model-based (labeled training data may be used to train models to define similarity between records).

It should be appreciated that other types of supervised classification models can be trained based on the training data 412, such as deep learning (feed-forward neural networks, CNNs, RNNs), SVMs/SVRs, regression-based methods, k nearest neighbours, kernel-based methods, decision tree and random forest-based approaches, Gaussian Mixture Models, Gaussian Processes, and other such approaches, as well as ensembles of these approaches and shared learning approaches such as multi-task and transfer learning.

In some embodiments, the machine learning models (e.g., model 414) can use active learning frameworks. For example, the model can selectively query an oracle for ground-truth labels for ambiguous examples that are hard to classify given the current training data (and avoid requiring a large amount of labeled data for training). Thus, the model iteratively improves and generates additional training data in the process by only querying for the "most difficult" and/or "most informative" examples. This can be achieved using learning frameworks such as membership query synthesis, pool-based sampling, stream-based sampling, among others and querying techniques such as balanced exploration/exploitation, expected change/error, exponentiated exploration, sampling, querying by committee or subspaces, variance reduction, conformal predictors, mismatch-first farthest-traversal, etc.

At block 114, the system determines whether one or more of the episodes of care are noisy or erroneous. A noise-removal engine can detect noisy/erroneous data and the affected data can either be corrected either manually, using rules or using machine learning models; or discarded depending on the severity of the noise/error. Noise may be defined as (a) one or more noisy attributes in an episode (e.g., negative payment amounts, invalid diagnosis/procedure codes, etc.) or (b) the entire episode being classified as noisy/erroneous (e.g., a newborn receiving geriatric care, a patient receiving care in two states concurrently likely as result of the member ID being misentered, etc.).

In some embodiments, the system uses a knowledge graph to identify noise in an episode of care. The rule set can include specific rules developed via a combination of medical domain knowledge and empirical data. For example, a rule can dictate that an episode of care is noisy because a male patient was given maternal care, a patient was given chemotherapy without any tumors being previously diagnosed, or if certain attributes are missing such as a patient identifier, etc. A rule set described herein can include a set of rule conditions, as well as the corresponding outputs, weights associated with each rule, etc.

Figure 4A:
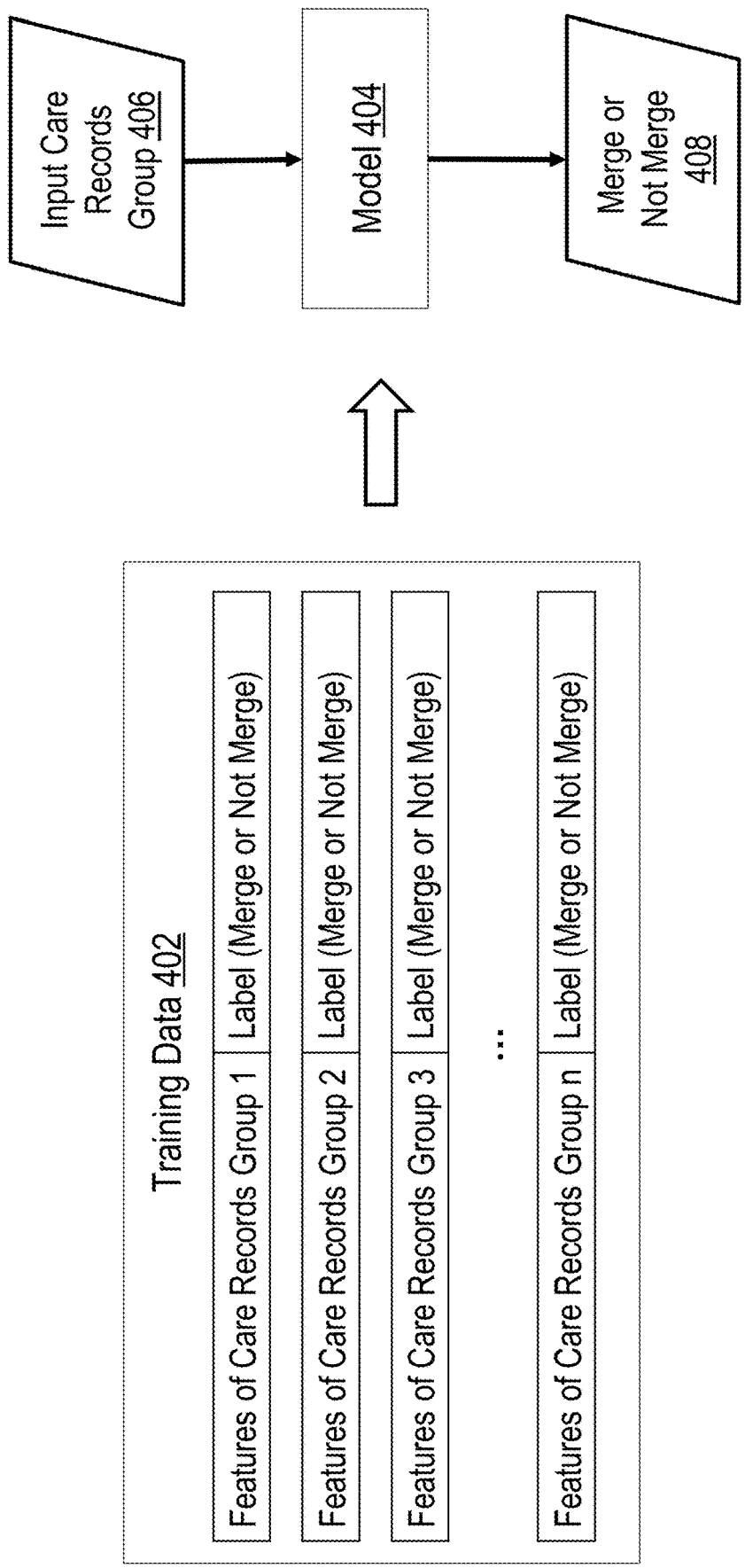
FIG. 4A illustrates an exemplary machine learning model for determining whether multiple care records should be merged together, in accordance with some embodiments.
Figure 4B:
FIG. 4B illustrates an exemplary machine learning model for determining how to fill Attribute A of an episode of care based on multiple care records to be merged, in accordance with some embodiments.
Figure 4C:
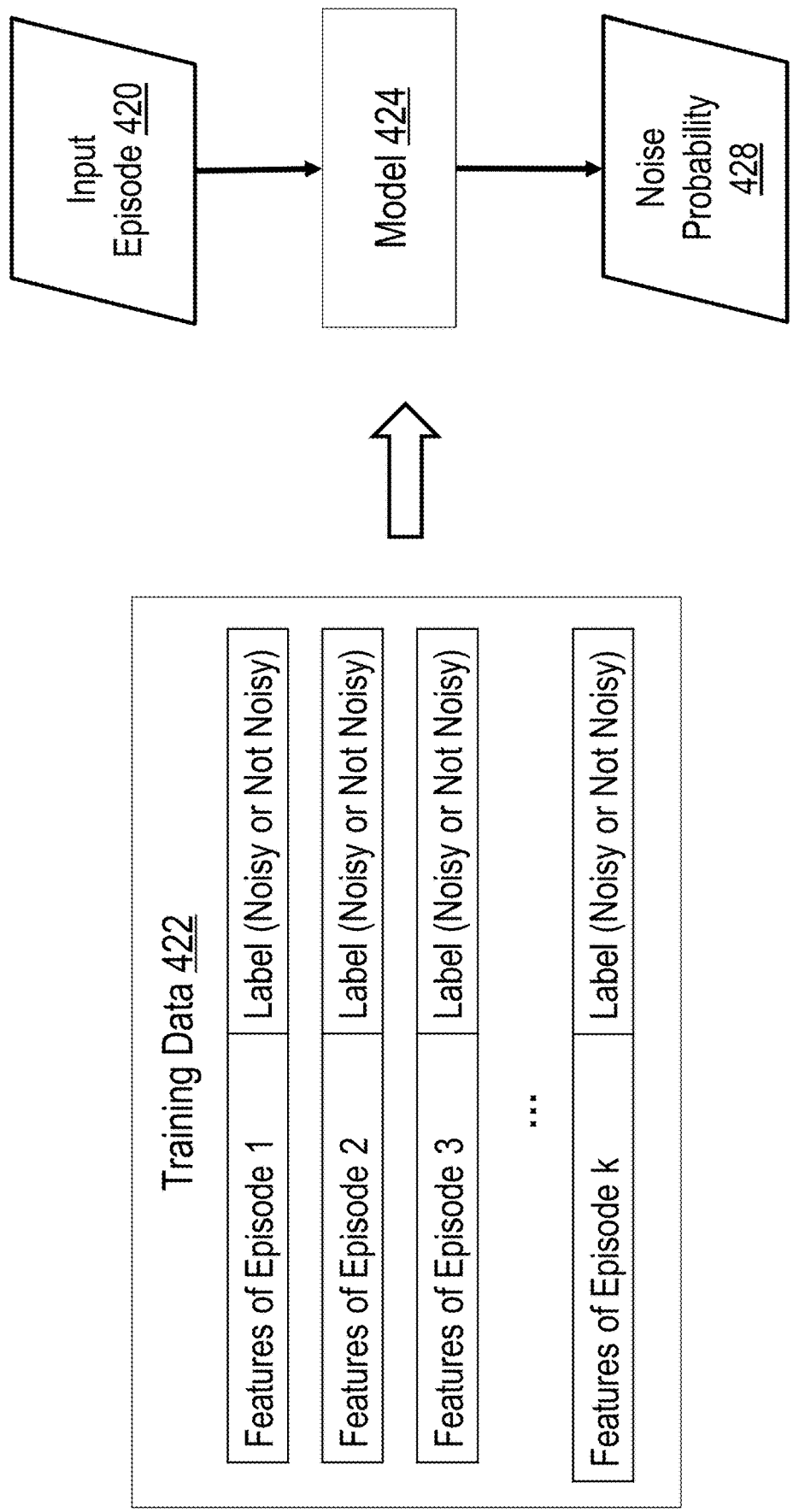
FIG. 4C illustrates an exemplary machine learning model for determining a noise probability of an input episode, in accordance with some embodiments.
Figure 7A:
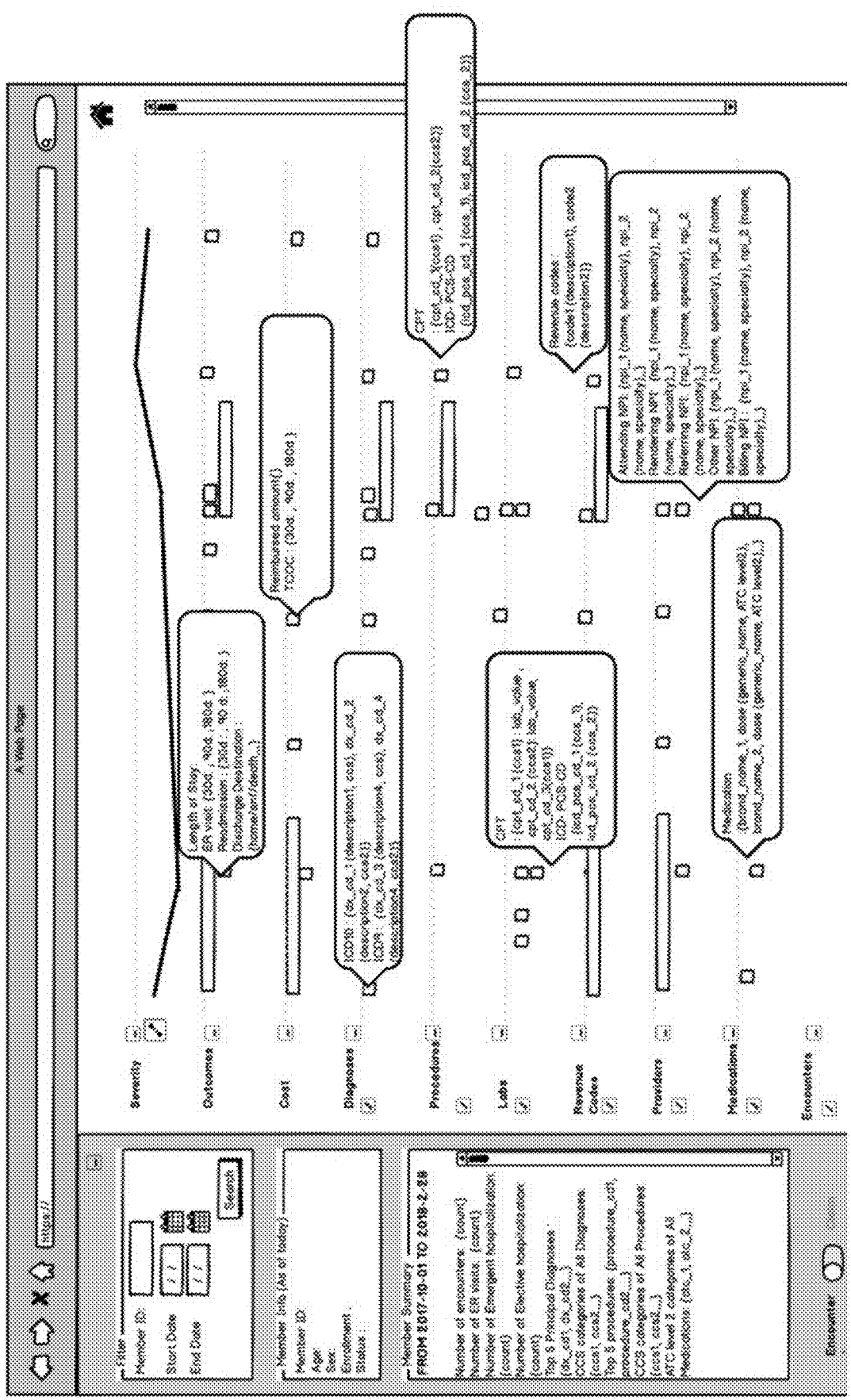
FIG. 7A illustrates a member view user interface, in accordance with some embodiments.
Figure 7B:
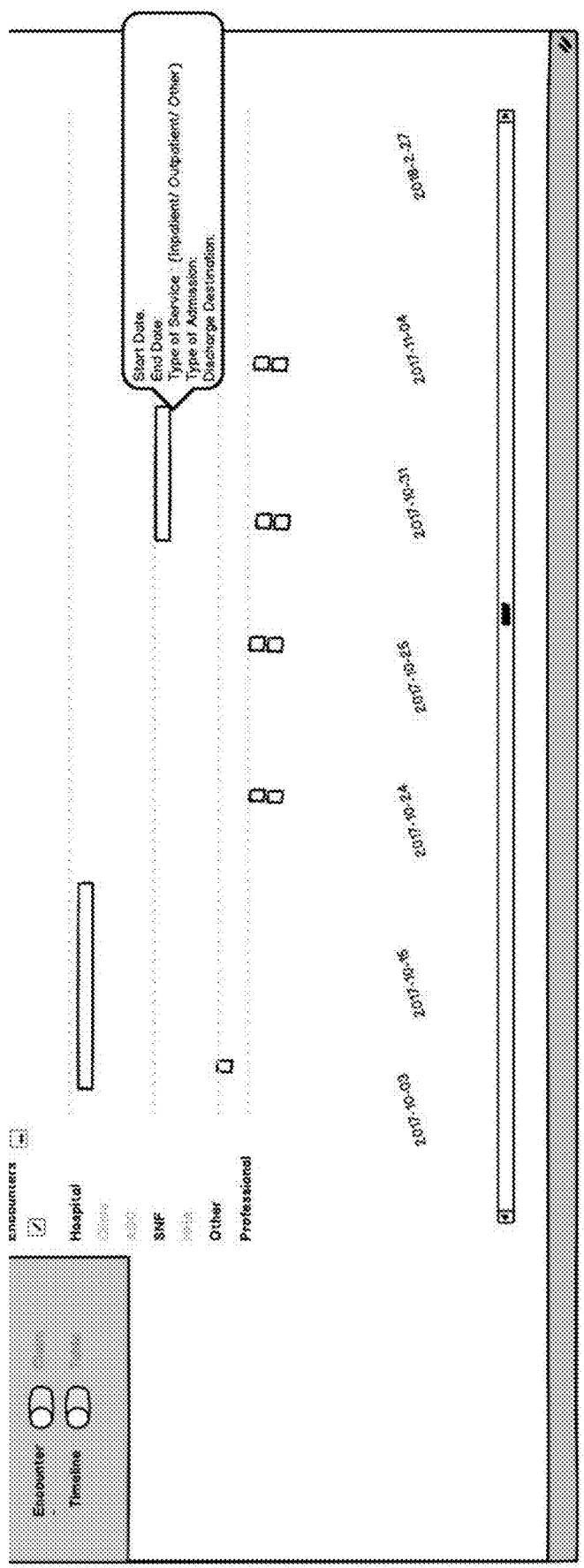
FIG. 7B illustrates a member view user interface, in accordance with some embodiments.
Figure 8B:
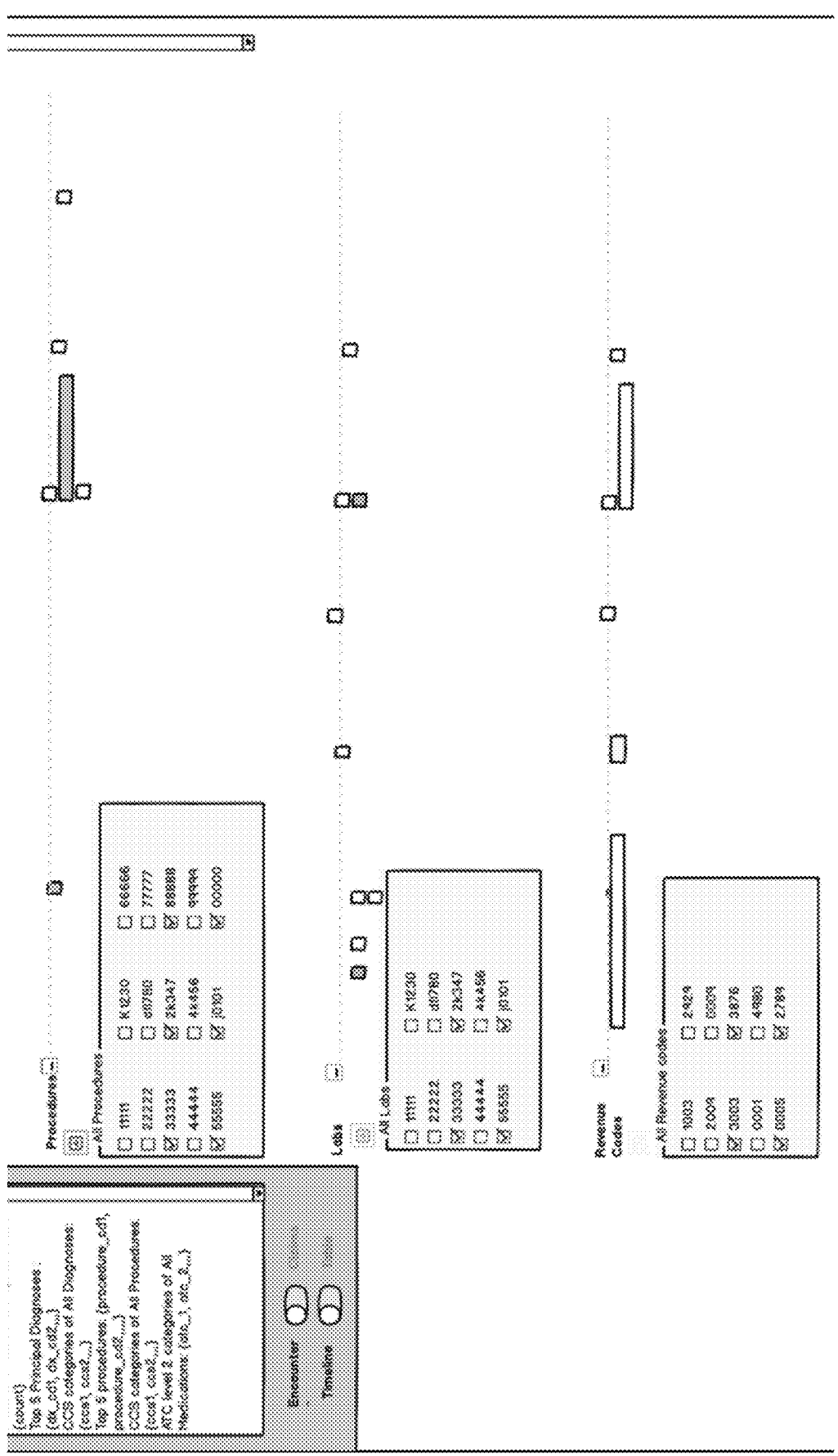
FIG. 8B illustrates a member view user interface with filtered attributes, in accordance with some embodiments.
Figure 8C:
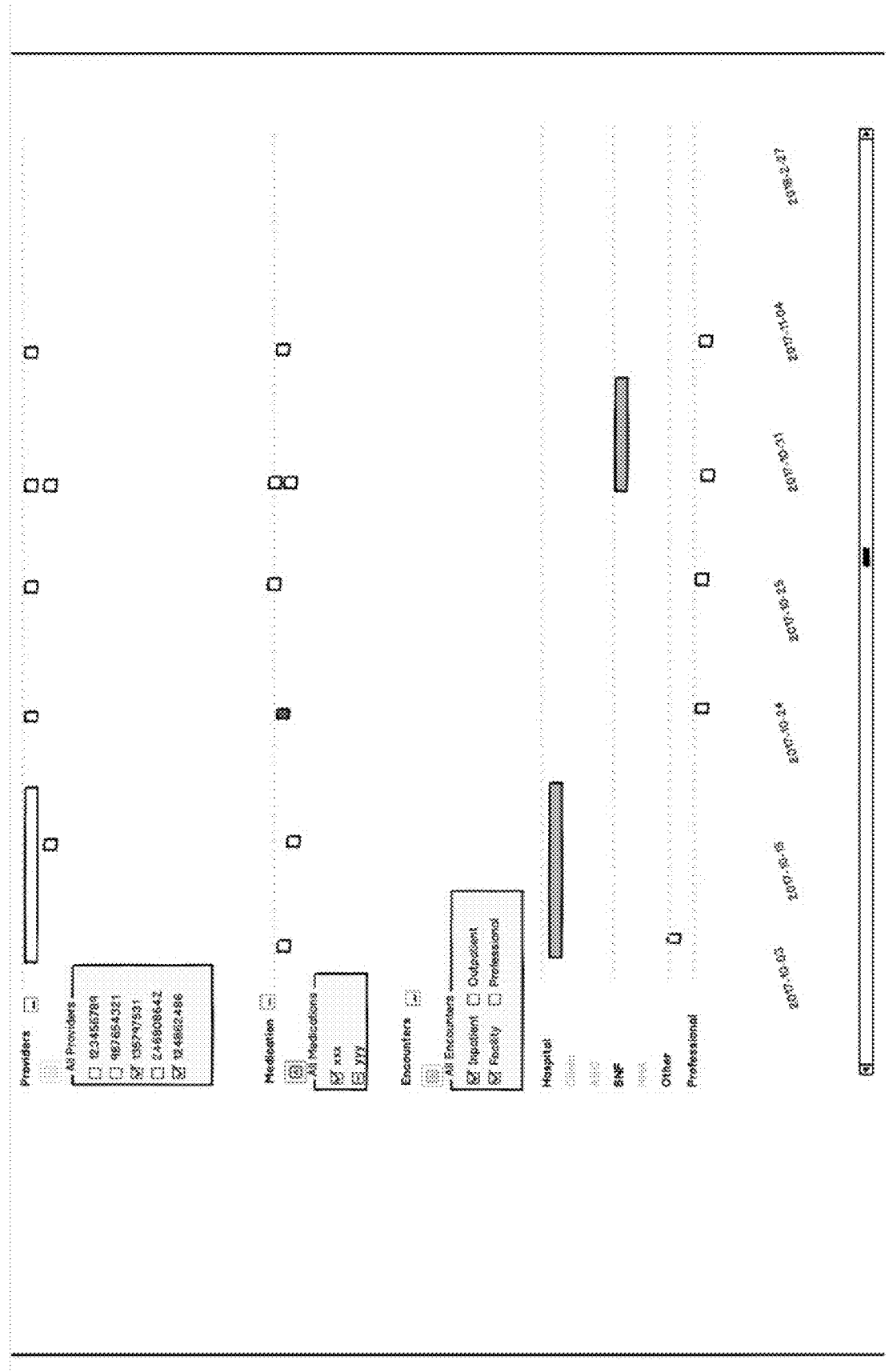
FIG. 8C illustrates a member view user interface with filtered attributes, in accordance with some embodiments.

In some embodiments, the system identifies noise in an episode of care using one or more machine learning models. FIG. 4C illustrates an exemplary machine learning model 424 for determining the probability of noise associated with an input episode. As depicted, the supervised learning model 424 is configured to receive an input episode 420 and provide an output 428 indicative of the noise probability in the input episode. For example, with reference to the example in FIG. 3C, the model 424 can receive as each of Episodes 1-6 and provide an output indicative of the noise probability.

In some embodiments, the features of an episode used in model 424 include some or all of available raw attributes in the care records from which the episode is constructed, including service/utilization dates, diagnostic/prognostic information, providers involved, place and setting of care, among others. Additional features such as longitudinal history of types of care received, trajectory of reimbursements and charges, trajectory of both raw physiological information (e.g., blood pressure) and derived risk scores such as heart rate variability, etc may also be used. These features may be used in addition to the features described above. These features are input into the model 424 to predict the probability of an episode (or one or more of its attributes) being noisy or erroneous. Features derived for multiple constituent records of care in an episode may be combined as stated above.

The machine learning model to identify noise, both in the attributes and the episode as a whole, may be supervised (training data including both episodes as well as labels for the episodes), semi-supervised (training data including labels only for some episodes) or unsupervised (training data has only episodes without labels).

In embodiments that use supervised learning, the model might be binary (predict 0/1 labels for noise at the attribute or episode level) or probabilistic (predict probabilities of noisiness). For each episode, the training data includes labels indicating whether or not each episode, or specific attributes in it, are noisy or erroneous (e.g., containing inconsistencies, anomalies, missing critical information). These labels can be generated manually. In some embodiments, the label for an episode is a binary value indicating the presence of noise/error in the episode as a whole. In some embodiments, the label for a training episode is a multi-dimensional data structure (e.g., vector) indicating the presence of noise/error for multiple attributes in the episode.

In various embodiments, the supervised model may be one of many possibilities described above (e.g., logistic/softmax regression, neural networks, tree-based methods, etc.). Supervised models that have multi-class outputs (to identify noise in various attributes in an episode) may be trained using the OVR (one vs the rest) method, or binary classifiers may be trained for each class and the output across all classes may be normalized.

In some embodiments, the system can extend the supervised learning framework (to a semi-supervised setting) by allowing the model to query an expert (i.e., an oracle) selectively for labels (i.e., whether or not an instance is an example of noise). Using active learning frameworks, the model uses a small amount of training data and iteratively improves its performance by selectively querying the expert for some of the most ambiguous/difficult instances. This can be achieved using learning frameworks such as membership query synthesis, pool-based sampling, stream-based sampling, among others and querying techniques such as balanced exploration/exploitation, expected change/error, exponentiated exploration, sampling, querying by committee or subspaces, variance reduction, conformal predictors, mismatch-first farthest-traversal, etc.

In some embodiments, the system can use unsupervised learning techniques to perform anomaly detection to identify records with spurious information, using unsupervised techniques such as minimum enclosing ball (MEB), one-class SVMs, clustering using k-means, k-nearest neighbours, hierarchical clustering and other similar clustering methods, matrix factorization based approaches (such as SVD, PCA, non-negative matrix factorization, etc.) to detect noisy or erroneous data. The system can perform additional feature extraction and processing on the raw data using sparse autoencoders, RBMs, etc. or generate temporal features using methods such as dynamic time warping, statistical aggregation methods, etc. before using these data in the machine learning models. Similar to the supervised and semi-supervised learning methods, these techniques may be applied at both the episode or attribute level.

Similar to the approaches described above, models may be trained to predict noise for individual episodes, individual attributes, or multiple attributes at a time using a shared structure learning framework (e.g., whether or not the diagnoses in an episode are noisy likely depend on the procedures and providers listed on the episode).

In some embodiments, the machine learning models may be time-series models (using techniques such as RNNs, LSTMs, and other sequence learning models). Thus, in such models, the noise probability for an episode E is predicted using features not just from episode E; instead, longitudinal features from upto T episodes in the past may be used. The system can determine that an episode needs to be removed if its noise exceeds a predefined threshold. For example, with reference to FIG. 3C, the system can determine that Episode 3's noise probability exceeds a predefined threshold and thus needs to be removed from the patient's episodes of care 302.

The system can determine that an episode needs to be revised if its noise exceeds a predefined threshold. For example, after identifying noise (in the form of missing or erroneous attribute values) in the data and removing the attribute values that are erroneous, the system can impute these values using a variety of methods. The system may use approaches based on single imputation (such as hot-deck, cold-deck, mean substitution, regression, etc.) or multiple imputation (such as multiple imputation by chained equations) to fill in noisy data. For example, the member's blood pressure on day 10 of an inpatient hospitalization might be imputed using the values on days 1-9 as well as days 11 onwards. These data might be continuous, binary or categorical values.

In some embodiments, the system may use a machine learning model similar to block 112 to replace or correct noisy values for attributes in episodes of care. Thus, given a noisy episode of care (i.e., an episode of care that has one or more noisy attributes, or an episode of care that is noisy in its entirety), the machine learning model may predict updated values for noisy attributes of care (similar to block 112).

At block 116, the system augments the one or more episodes of care with additional metadata. The additional metadata can be derived from secondary processing of the input tables or other sources, including the use of these tables and other sources in both their raw form and in the form of the episodes of care. Similarly, episodes that involve multiple providers offering services contain information about the primary provider(s) that were likely responsible for the episode.

Some examples are:

Compared to ICD codes for diagnoses available in raw records, episodes of care can be augmented with easily interpretable high-level information such as the chronic conditions identified during the episode, the anatomical regions they might affect.

Similar to diagnoses, procedure codes can be converted to high-level information about the type of surgery, the anatomical region it affects, the recommended followup care, the diagnoses/events that led to the procedure, etc.

Augmenting episodes with longitudinal information such as the outcomes associated with them (surgeries that lead to complications, diagnoses that were treated with surgeries, etc.)

The medical 'status' of the patient, defined using a risk-score or measure of 'health' using any arbitrary measure that could be based on their past/future diagnoses, prognoses, procedures, etc. including but not limited to processes used to risk-adjust patients such as RAF scores, etc.

Attributing the episode of care to providers that were primarily responsible for the episode of care (e.g., for complex care episodes that may be collected or archived as multiple records, identifying the primary attending/rendering physicians, etc.), and further augmenting the providers with additional metadata such as their medical training information, statistics about their typical outcomes, etc.

Adding additional context (e.g., whether an episode followed by another episode corresponded to transfer discharge or a home discharge followed by a readmission etc.)

In some embodiments, episodes of care may be augmented with additional metadata using machine learning models.

Supervised machine learning models may be used in the examples described with respect to FIG. 5C to add continuous, binary or multi-class high-level metadata to episodes beyond the attributes that already exist. For example, a multi-class model may be used to identify high-level surgeries (such as stent placement, knee replacement, etc.) using raw procedure codes (e.g., ICD, HCPCS, AAPC, etc.). Raw diagnosis codes, clinical data, EHR data may similarly be used to identify chronic conditions, comorbidities, high-risk events, etc. As another exemplary example, supervised models may be trained to identify cohorts of patients that are stratified based on their risk for certain events of interest (e.g., mortality, fall-risk for elderly patients, heart attack, etc.). These models may be trained using labeled data, which may be featurized using techniques described under the "Computational and Algorithmic Complexity of Joins" Section, using modeling techniques similar to the ones described under the "Computational and Algorithmic Complexity of Joins" Section.

Unsupervised machine learning models may be used in some embodiments to generate high-level metadata for episodes of care. These include techniques such as, Summarization techniques, applied to textual data such as doctor's notes, Topic modeling techniques applied to descriptions of diagnosis codes, procedure codes, etc. to discover latent high-level topics in the diagnoses/procedures across all patients.

At block 118, the system generates patient profiles. For each patient, the corresponding patient-specific profile comprises all episodes for the patient. The episodes can be organized into a patient timeline/trajectory. The patient-specific profile can further comprise metadata (e.g., from block 116) characterizing the patient at different points in time.

Figure 3E:
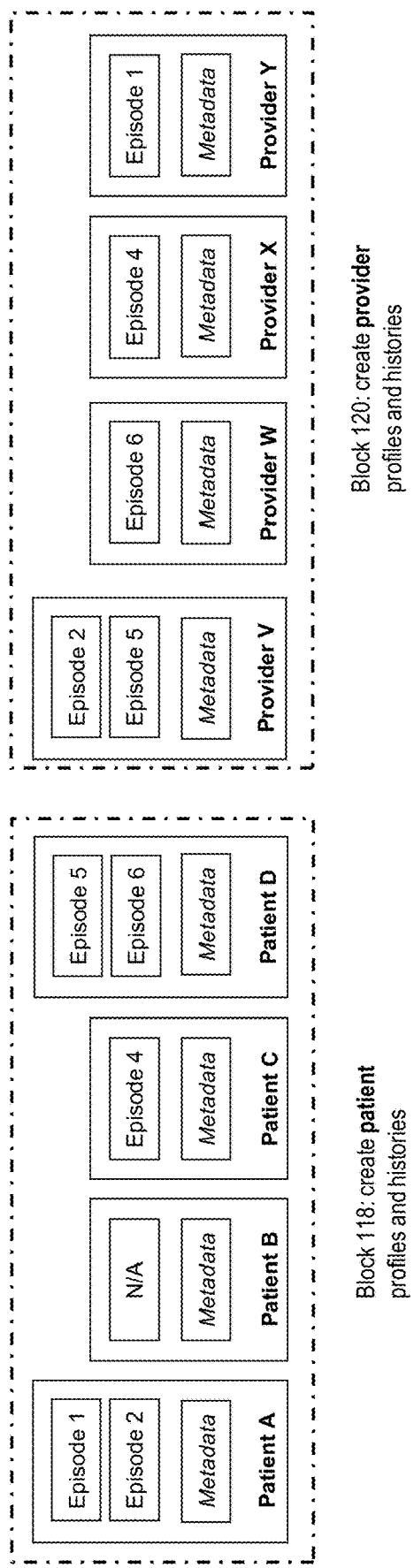
FIG. 3E illustrates exemplary patient profiles and provider providers, in accordance with some embodiments.

FIG. 3E depicts a set of exemplary patient profiles, in accordance with some embodiments. As an example, for Patient A, episodes 1 and 2 are included in the profile. The episodes can be organized into a patient timeline/trajectory. Thus, the patient-specific profile provides a longitudinal view of all episodes of care and metadata relevant to the patient. The profile allows visualization of a patient's evolving health through the episodes and provide quick answers to questions about the patient such as:

How many episodes a patient had within a time period;

How many specific types of episodes (e.g., for a specific specialty, for a specific diagnosis, with a specific provider) a patient has had;

Statistics for a given episode (e.g., total cost of care, outcome)

Statistics for multiple episodes over time (e.g., trends over time, occurrence/reoccurrence of conditions, readmissions)

Patterns of patient health (e.g., disease trajectories)

Changes in drug prescriptions and treatments for a patient

Metadata related to a patient (e.g., preferred geographical region for care, chronic conditions)

At block 120, the system generates provider profiles. For each provider, the corresponding provider profile comprises all episodes for the provider. The episodes can be organized into a patient timeline/trajectory. The provider-specific profile can further comprise metadata (e.g., from block 116) characterizing the provider at different points in time.

FIG. 3E depicts a set of exemplary provider-specific profiles, in accordance with some embodiments. As an example, for Provider V, episodes 2 and 5 are included in the profile. The episodes can be organized into a provider timeline/trajectory. Thus, the provider-specific profile provides a longitudinal view of all episodes of care and metadata relevant to the provider. The profile allows visualization of a provider's evolving practice through the episodes and provide quick answers to questions about the patient such as:

The number of patients treated by a provider

Categories of patients treated by a provider (e.g., grouped by conditions, demographics, type of treatment)

Quality of care of the provider (e.g., rates of adverse outcomes, morbidity)

Primary provider experience and volume and how these change over time

Primary Provider billing and reimbursement, and how these change across time

Insurance plans accepted by the provider over time

Willingness to take on new patients etc.

In some embodiments, the augmented episodes of care (e.g., block 116) are stored as compact objects, which may include Protocol Buffer, Avro or Thrift objects, that can be stored in standard SQL/NoSQL databases as well as in other file and data formats, can be readily serialized, can be used with systems optimized for simultaneous reads by multiple processes, support data provenance, support encryption, etc. These objects expose the data related to patients and providers and their episodes through attributes that can be directly accessed in their post-processed form and expose a common interface of these attributes that can be used by higher-level analyses; even as the way these objects are created in preceding steps might change (i.e., the objects offer an abstraction of how the processing is done, and allow higher-level analyses to be able to reference attributes for visualization and analyses, freed of details of the original input data and how the various processing steps upstream were performed).

Technical Improvements and Practical Applications

The intelligent healthcare data fabric system presents significant improvements to existing systems in the technical field and further improves the functioning of a computer system. Exemplary technical improvements of the system are provided below.

The present system is independent of coding formats or representations across payers and providers. The system is inherently agnostic to the specific coding formats and representations for raw healthcare data used by payers and providers. Instead, after aggregating raw data from various data sources across different players and providers, the system leverages a technical pipeline (including machine learning techniques and rule sets) to generate high-level representations (e.g., episodes of care, patient-specific profiles, and provider-specific profiles). This way, the system is robust to changing data formats and mappings in the raw data.

The present system separates high-level analyses from low-level data engineering efforts. The present system generates high-level data constructs corresponding to natural units of analysis (e.g., episodes, patient-specific profiles, provider-specific profiles). These high-level data constructs shield users from having to engage with raw data. These high-level data constructs can be organized compactly and expose useful information for patients and providers and the episodes of care associated with them.

The present system enriches the patient, provider and episode of care data with high-level metadata. The attributes in the high-level data constructs (e.g., patient-specific profiles, provider-specific profiles, and episodes of care) are significantly easier to interpret and analyze as a result of their being enriched with derived high-level metadata. This architecture has the added benefit of ensuring consistency in best practices and ETL processes across various end-user applications and payer/provider systems. For example, compared to ICD codes for diagnoses and procedures available in raw records, episodes of care contain easily interpretable high-level information such as the chronic conditions identified during the episode, the anatomical regions they might affect, the procedures that were performed during the episodes, etc. Similarly, episodes that involve multiple providers offering services contain information about the primary provider(s) that were likely responsible for the episode.

The proposed system has a low barrier to usability. The system is platform-independent. The data constructs for patients, providers and episodes of care can be analyzed in various operating systems (e.g., Linux, Mac, Windows, etc.) using several common programming environments (e.g., Python, JAVA, C, JavaScript, etc.). This enables the use of the proposed system in both back-end systems (running JAVA, C, Python, etc.) as well as resource-limited user-facing servers (running Python, JavaScript, etc.).

The system allows easy serialization and deserialization. The data constructs support fast serializable/deserializable into lightweight byte-code representations that can be stored and transported easily. Thus, it is possible to store/cache the data constructs in a space-efficient manner due to their lightweight nature. The serialized data constructs are easily encryptable, using a variety of standard encryption standards/algorithms. This feature is especially useful for high-value Protected Health Information (PHI).

The system supports interoperability between arbitrary data formats. In particular, the proposed system can ingest data in arbitrary, proprietary and/or open source data formats (e.g., X12, FHIR, etc.) and similarly also produce output data in these same formats. This is supported through input/output adapters and modules that import and export data into and out of the data fabric. The input and output formats are not tightly coupled; in that data can be ingested from any supported format into the data fabric and then output from the data fabric into any output format.

The intelligent healthcare data fabric system further includes numerous practical applications. The high-level data constructs greatly simplify downstream analytics and visualization operations that would otherwise have been cumbersome with raw healthcare data. The consolidation of all records, and therefore diagnoses, prognoses, procedures, provider information, charges, etc., relevant to an episode of care into a single data representation provides a natural framework in which these episodes of care can be analyzed. Similarly, the patient and provider profiles provide easy access to the complete longitudinal history associated with each patient/provider, thus greatly simplifying patient and provider level analyses.

For example, consider calculating the average cost of cardiac surgery in New York. The system can first identify all patients in New York (using patient metadata for the episodes) who received cardiac surgeries (using episode service data), and average the reimbursements (using episode cost data) associated with them. As another example, consider calculating the total cost of care associated with a patient over a given year; due to the easy availability of all episodes of care associated with a patient, this calculation ends up being a simple iteration through all episodes of interest and aggregating reimbursements.

Further, the system can use the episode data to train a plurality of machine-learning models. For example, the system can use the episode data to train a prediction model configured to receive information about a new patient/provider and output a prediction (e.g., a predicted risk of an outcome, a predicted likelihood of a diagnosis, a predicted response to a treatment, a predicted cost of care). As another example, the episode data can be used to train a classification model configured to receive information about a new patient/provider and output a classification result (e.g., a label or category). As another example, the system can use episode data to train unsupervised machine-learning models (e.g., clustering) to identify patterns and make new discoveries from the data. In some embodiments, a model can be trained to study a specific patient type (e.g., female patients in their 70-80s in New York), a provider type, etc., and the episode data can be easily selected to be included in the training dataset based on the desired attributes accordingly. By taking noisy, fragmented, incomplete data and creating patient profiles and provider profiles, the system allows for easy modeling, analytics, and inference.

The machine-learning models described herein include any computer algorithms that improve automatically through experience and by the use of data. The machine-learning models can include supervised models, unsupervised models, semi-supervised models, self-supervised models, etc. Exemplary machine-learning models include but are not limited to: linear regression, logistic regression, decision tree, SVM, naive Bayes, neural networks, K-Means, random forest, dimensionality reduction algorithms, gradient boosting algorithms, etc.

The system supports the visualization of patient and provider profiles through a graphical user interface (an exemplary member view is shown in FIGS. 7A-7B and FIGS. 8A-C). Users can enter identifiers such as member or provider IDs, and view the complete longitudinal history for a patient or provider. The view may include information about the episode(s) of care associated with the member or provider such as longitudinal outcomes after each episode, payment information, physiological information, medications, diagnoses, procedures, etc. These information may be presented in tabular/text format, or graphically using plots or figures.

In some embodiments, the visualization may include higher level derived information related to the member or provider. For example, a severity score may be derived based on diagnoses, procedures, metabolic and physiological data, etc. These scores may further be derived using methodology that compares the profile a patient/provider with profiles of other patients/providers in their demographic, physiological, socio-economic, geographic, etc. cohorts and establishes a metric to quantify a patient's health or a provider's performance.

Figure 9:
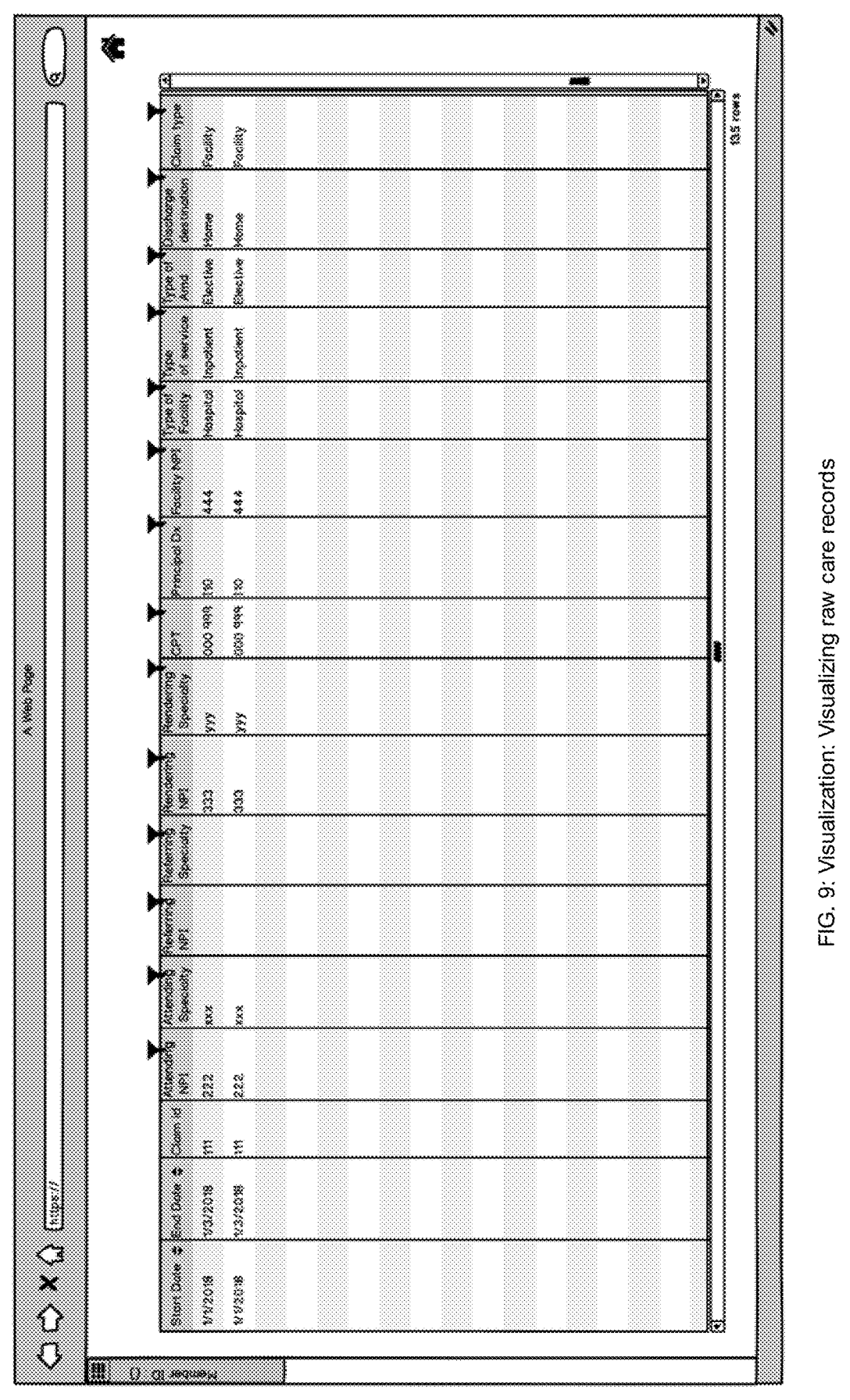

In some embodiments, the raw care records that constitute an episode may also be visualized, as shown in FIG. 9. The care records may further be filtered based on specific attributes of interest (as shown in FIG. 10).

The attributes included in the visualization include high-level metadata related to the attribute values. For example, hovering over diagnoses made during an episode may show information about chronic conditions that relate to the diagnosis, its prevalence in the population, possible treatments for any treatable conditions, etc.

The visualization allows the user to filter or highlight attributes down to certain values of interest. For example, in the procedure tab for a member, all procedures related to a knee replacement surgery may be highlighted through a drop-down tab.

In some embodiments, machine learning models may be used to 'summarize' patients/providers using dimensionality reduction techniques, such as PCA, manifold learning, tSNE, sparse auto-encoders, matrix factorization, etc. Thus, all available information in an episode may be used to project a patient or provider on an arbitrary manifold with a pre-specified number of dimensions. In some embodiments, the number of dimensions may be 1 (thus, the attributes for a patient or provider are projected to a single real number) and this projected value may be used as the severity score for a patient.

In some embodiments, the visualization may be used to compare patients or providers in terms of their longitudinal histories. The interface may be used to display raw values of attributes for two or more patients side-by-side. The comparison may be extended to larger cohorts, where the value for each attribute is shown along with statistical information. For example, for a specialist visit to a cardiologist, the visualization may display the (a) payment information as percentile values relative to payments in a similar cohort, (b) diagnosis, procedure, medication information along with probability values that represent how likely the are to occur in other knee replacement episodes, (c) longitudinal outcomes such as ER visits and hospitalizations following the episode along with probabilities that compare them the rate of these outcomes in the cohort, etc.

In some embodiments, the visualization may be used to support treatment or intervention decisions by visualizing the results of one of many possible actions. In particular, at each episode, the effect of a certain medication, procedure, intervention, etc. may be predicted by using machine learning models trained on similar episodes for similar patients. The measure of similarity may be defined using functional metrics for episodes (cardiologist specialist visits, PCI surgery, etc.) and demographic, physiological, clinic, etc. metrics for patients (similar age, vitals, hospitalization history, etc.). Thus, the machine learning model may predict values for certain outcomes of interest such as the rates of ER visits and hospitalizations, the patient's vitals, cost of care, etc. These predictions can then be visualized, longitudinally, using the proposed embodiment. As another example, the system can identify similar episodes that involve the same treatment, and evaluate the outcomes of these episodes to determine the effect of the treatment.

The intelligent healthcare data fabric system has broad utility, including but not limited to machine learning-based analyses for care delivery and an appreciation and optimization of healthcare delivery and economics.

The intelligent healthcare data fabric system further affects treatments of patients. In some embodiments, the system generates and implements a care and treatment plan based on the episode data in patient profiles and/or provider profiles. The care and treatment plan can include recommendation and coordination of one or more treatments over time. A treatment can include a medication (e.g., a prescribed drug at a specific dosage), a procedure, an intervention, etc. The treatment can be identified based on the patient's patient profile, such as how the patient's condition has evolved over time and how the patient has responded to different treatments over time. In some embodiments, the plan is determined based on predefined rules and conditions. For example, if the patient profile shows positive responses to the same treatment, the system can include the treatment in the care and treatment plan. In some embodiments, the plan is determined based on machine-learning models described herein. The care and treatment plan can then be implemented by medical professionals or automatically by controlling one or more medical devices. The patient profile can generally allow for efficient and effective management of patient care.

In some embodiments, the intelligent healthcare data fabric system can be used for utilization review, which allows payers, particularly health insurance companies to manage the cost of health care benefits by assessing its appropriateness before providing the care. For example, the system can evaluate whether a proposed treatment should be authorized based on the patient's patient record for determining if there is fraud/overtreatment/inappropriateness. For example, the system can compare the proposed treatment with the patient's condition to determine whether the proposed treatment is targeted at addressing the patient's condition. In some embodiments, the system inputs the proposed treatment into a trained machine-learning model, which is trained based on episode data, to make the determination. Similarly, the system can be used to evaluate and process medical claims. For example, the system can determine that the claim is abnormal based on the patient record and approve or deny payment accordingly. In some embodiments, the system inputs the claim into a trained machine-learning model, which is trained based on episode data, to make the determination.

In some embodiments, the intelligent healthcare data fabric system can be used for call center support. A patient profile generated using techniques described herein is helpful any time a user needs to quickly understand a patient, for example, when he or she is serving real-time support requests from the patient.

FIG. 11 illustrates process 1100 for generating a patient profile of a patient, according to various examples. Process 1100 is performed, for example, using one or more electronic devices implementing a software platform. In some examples, process 1100 is performed using a client-server system, and the blocks of process 1100 are divided up in any manner between the server and a client device. In other examples, the blocks of process 1100 are divided up between the server and multiple client devices. Thus, while portions of process 1100 are described herein as being performed by particular devices of a client-server system, it will be appreciated that process 1100 is not so limited. In other examples, process 1100 is performed using only a client device (e.g., user device 100) or only multiple client devices. In process 1100, some blocks are, optionally, combined, the order of some blocks is, optionally, changed, and some blocks are, optionally, omitted. In some examples, additional steps may be performed in combination with the process 1100. Accordingly, the operations as illustrated (and described in greater detail below) are exemplary by nature and, as such, should not be viewed as limiting.

At block 1102, an exemplary system (e.g., one or more devices) receives a plurality of care records; at block 1104, the system determines, based on a first machine learning model, that the plurality of care records are to be merged into an episode, wherein the episode is a predefined data representation comprising a predefined collection of data fields; at block 1106, the system identifies, from the plurality of care records, a plurality of attribute values corresponding to a particular attribute; at block 1108, the system determines, based on a second machine learning model, an aggregated attribute value based on the plurality of attribute values; at block 1110, the system updates, based on the aggregated attribute value, a data field of the episode; at block 1112, the system adds the episode to the patient profile, wherein the patient profile comprises a plurality of episodes associated with the patient.

Figure 12:
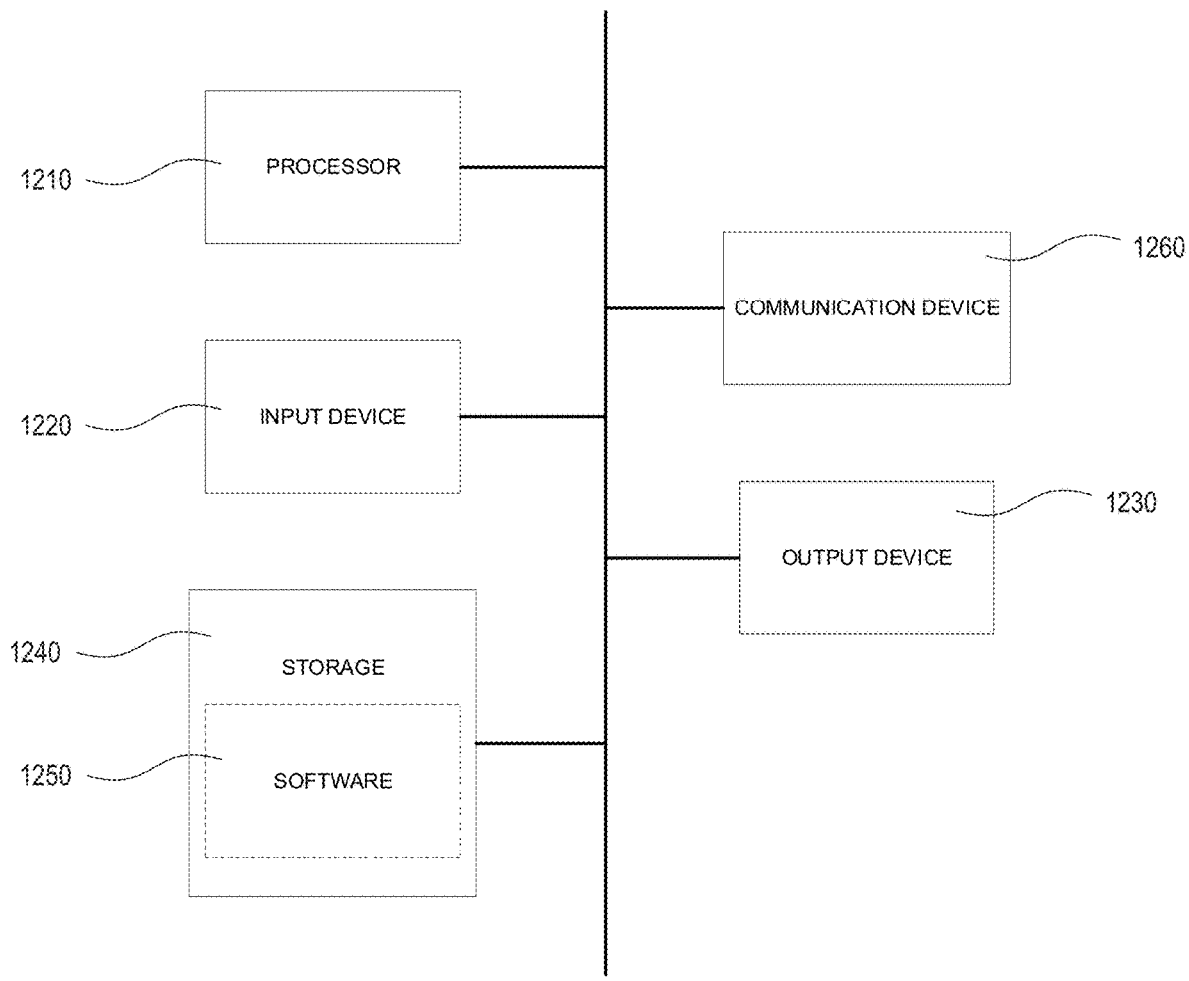
FIG. 12 illustrates an exemplary electronic device in accordance with some embodiments.

FIG. 12 illustrates an example of a computing device in accordance with one embodiment. Device 1200 can be a host computer connected to a network. Device 1200 can be a client computer or a server. As shown in FIG. 12, device 1200 can be any suitable type of microprocessor-based device, such as a personal computer, workstation, server or handheld computing device (portable electronic device) such as a phone or tablet. The device can include, for example, one or more of processor 1210, input device 1220, output device 1230, storage 1240, and communication device 1260. Input device 1220 and output device 1230 can generally correspond to those described above, and can either be connectable or integrated with the computer.

Input device 1220 can be any suitable device that provides input, such as a touch screen, keyboard or keypad, mouse, or voice-recognition device. Output device 1230 can be any suitable device that provides output, such as a touch screen, haptics device, or speaker.

Storage 1240 can be any suitable device that provides storage, such as an electrical, magnetic or optical memory including a RAM, cache, hard drive, or removable storage disk. Communication device 1260 can include any suitable device capable of transmitting and receiving signals over a network, such as a network interface chip or device. The components of the computer can be connected in any suitable manner, such as via a physical bus or wirelessly.

Software 1250, which can be stored in storage 1240 and executed by processor 1210, can include, for example, the programming that embodies the functionality of the present disclosure (e.g., as embodied in the devices as described above).

Software 1250 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1240, that can contain or store programming for use by or in connection with an instruction execution system, apparatus, or device.

Software 1250 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1200 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1200 can implement any operating system suitable for operating on the network. Software 1250 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A computer-implemented method for generating a care and treatment plan for a patient, comprising:
   (a) receiving an initial series of care records;
   (b) generating a first plurality of care data groups based on the initial series of care records, each care data group comprising at least two care records from the initial series;
   (c) generating a feature vector for each care data group of the first plurality of care data groups to obtain a first plurality of feature vectors;
   (d) inputting each feature vector of the first plurality of feature vectors into a trained machine-learning model to determine if a care data group is to be merged into a single medical episode to identify a new series of care records, medical episodes, or a combination thereof;
   (e) generating a second plurality of care data groups based on the new series, each care data group comprising at least: two care records, two medical episodes, or a care record and a medical episode;
   (f) generating a feature vector for each care data group of the second plurality of care data groups to obtain a second plurality of feature vectors;
   (g) inputting each feature vector of the second plurality of feature vectors into the trained machine-learning model to determine if a care data group is to be merged into a single medical episode to update the new series of care records, medical episodes, or a combination thereof;
   (h) repeating steps (e)-(g) zero or more times using the new series to identify a final series of medical episodes, wherein each medical episode of the final series of medical episodes corresponds to one or more care records in the initial series of care records; and
   (i) creating a patient profile for the patient, the patient profile comprising at least a subset of the final series of medical episodes; and
   (j) generating the care and treatment plan for the patient based on the patient profile by:
      training one or more machine-learning models using a plurality of medical episodes corresponding to patients similar to the patient; and
      generating the care and treatment plan based on the trained one or more machine-learning models and one or more medical episodes in the patient profile.

2. The method of claim 1, wherein the care and treatment plan comprises:
   coordination, recommendation, or administration of one or more treatments or care services for the patient.

3. The method of claim 2, wherein the one or more treatments or care services comprise: a medication, a procedure, an intervention, a test, a service, a lifestyle change, a behavior, a diagnosis, a prognosis, or a combination thereof.

4. The method of claim 1, further comprising: evaluating a medical claim or a proposed treatment based on the patient profile for eligibility, prior authorization, or approval.

5. The method of claim 1, wherein the one or more machine-learning models comprise a predictive machine-learning model; and wherein determining the care and treatment plan comprises:

determining an effect of care and treatment based on the trained predictive machine-learning model.

6. The method of claim 5, wherein the predictive model is configured to output a predicted outcome of the care and treatment.

7. The method of claim 1, wherein repeating steps (e)-(g) comprises repeating steps (e)-(g) until none of the care data groups can be merged.

8. The method of claim 1, wherein the machine-learning model is trained using a first training dataset comprising:
   features of a plurality of groups of care records; and
   for each group of care records, a label indicating whether or not the respective group of care records can be merged.

9. The method of claim 8, further comprising: obtaining a label corresponding to a group of care records by querying a user using an active learning framework.

10. The method of claim 1, wherein the machine-learning model is a first machine-learning model, the method further comprising:
   after identifying a care data group that is to be merged into a single medical episode:
      identifying a plurality of attribute values corresponding to an attribute from the care data group;
      determining, based on a second machine-learning model, an aggregated attribute value based on the plurality of attribute values;
      merging the care data group by generating a medical episode and assigning the aggregated attribute value to a data field of the generated medical episode.

11. The method of claim 10, wherein the second machine-learning model is trained using a second training dataset comprising:
   features of a plurality of groups of care records; and
   for each group of care records, an aggregate attribute value of the particular attribute.

12. The method of claim 11, further comprising: obtaining a label corresponding to a group of care records and one or more attributes by querying a user using an active learning framework.

13. The method of claim 10, further comprising: determining, based on a third machine-learning model, one or more noise probabilities for the generated episode.

14. The method of claim 13, further comprising: updating the generated medical episode based on the one or more noise probabilities.

15. The method of claim 1, further comprising: adding an episode of the final series of medical episodes to a provider profile, wherein the provider profile comprises a plurality of episodes associated with a provider.

16. The method of claim 1, further comprising: adding an episode of the final series of medical episodes to a patient profile, wherein the patient profile comprises a plurality of episodes associated with a patient.

17. The method of claim 1, wherein the series of care records comprises health care claims data, clinical (EHR) data, wearable data, self-reported patient data, omics data, imaging data, social determinants of health data, demographic data, administrative data, economic data, device data, lab data, or any combination thereof.

18. The method of claim 1, further comprising: augmenting the series of data records with provider metadata and patient metadata.

19. A system for generating a care and treatment plan for a patient, comprising:
   one or more processors;
   a memory; and
   one or more programs, wherein the one or more programs are stored in the memory and configured to be executed by the one or more processors, the one or more programs including instructions for:
   (a) receiving an initial series of care records;
   (b) generating a first plurality of care data groups based on the initial series of care records, each care data group comprising at least two care records from the initial series;
   (c) generating a feature vector for each care data group of the first plurality of care data groups to obtain a first plurality of feature vectors;
   (d) inputting each feature vector of the first plurality of feature vectors into a trained machine-learning model to determine if a care data group is to be merged into a single medical episode to identify a new series of care records, medical episodes, or a combination thereof;
   (e) generating a second plurality of care data groups based on the new series, each care data group comprising at least: two care records, two medical episodes, or a care record and a medical episode;
   (f) generating a feature vector for each care data group of the second plurality of care data groups to obtain a second plurality of feature vectors;
   (g) inputting each feature vector of the second plurality of feature vectors into the trained machine-learning model to determine if a care data group is to be merged into a single medical episode to update the new series of care records, medical episodes, or a combination thereof;
   (h) repeating steps (e)-(g) zero or more times using the new series to identify a final series of medical episodes, wherein each medical episode of the final series of medical episodes corresponds to one or more care records in the initial series of care records; and
   (i) creating a patient profile for the patient, the patient profile comprising at least a subset of the final series of medical episodes; and
   (j) generating the care and treatment plan for the patient based on the patient profile by:
      training one or more machine-learning models using a plurality of medical episodes corresponding to patients similar to the patient; and
      generating the care and treatment plan based on the trained one or more machine-learning models and one or more medical episodes in the patient profile.

20. A non-transitory computer-readable storage medium storing one or more programs for generating a care and treatment plan for a patient, the one or more programs comprising instructions, which when executed by one or more processors of an electronic device, cause the electronic device to:
   (a) receive an initial series of care records;
   (b) generate a first plurality of care data groups based on the initial series of care records, each care data group comprising at least two care records from the initial series;
   (c) generate a feature vector for each care data group of the first plurality of care data groups to obtain a first plurality of feature vectors;
   (d) input each feature vector of the first plurality of feature vectors into a trained machine-learning model to determine if a care data group is to be merged into a single medical episode to identify a new series of care records, medical episodes, or a combination thereof;

(e) generate a second plurality of care data groups based on the new series, each care data group comprising at least: two care records, two medical episodes, or a care record and a medical episode;
(f) generate a feature vector for each care data group of the second plurality of care data groups to obtain a second plurality of feature vectors;
(g) input each feature vector of the second plurality of feature vectors into the trained machine-learning model to determine if a care data group is to be merged into a single medical episode to update the new series of care records, medical episodes, or a combination thereof;
(h) repeat steps (e)-(g) zero or more times using the new series to identify a final series of medical episodes, wherein each medical episode of the final series of medical episodes corresponds to one or more care records in the initial series of care records; and
(i) create a patient profile for the patient, the patient profile comprising at least a subset of the final series of medical episodes; and
(j) generate the care and treatment plan for the patient based on the patient profile by:
training one or more machine-learning models using a plurality of medical episodes corresponding to patients similar to the patient; and
generating the care and treatment plan based on the trained one or more machine-learning models and one or more medical episodes in the patient profile.

* * * * *